(12) United States Patent
Francischelli et al.

(10) Patent No.: US 8,221,411 B2
(45) Date of Patent: Jul. 17, 2012

(54) SYSTEMS AND METHODS FOR CARDIAC TISSUE ELECTROPORATION ABLATION

(75) Inventors: David Francischelli, Anoka, MN (US);
Mark Stewart, Lino Lakes, MN (US);
Jinback Hong, Maple Grove, MN (US);
Vladimir Nikolski, Blaine, MN (US);
Cushing Hamlen, Edina, MN (US);
Daniel Cheek, Plymouth, MN (US);
Matthew Bonner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 719 days.

(21) Appl. No.: 12/331,004

(22) Filed: Dec. 9, 2008

(65) Prior Publication Data
US 2010/0023004 A1    Jan. 28, 2010

Related U.S. Application Data

(60) Provisional application No. 61/084,149, filed on Jul. 28, 2008.

(51) Int. Cl.
*A61B 18/18* (2006.01)

(52) U.S. Cl. ........................................ 606/41

(58) Field of Classification Search ........... 606/41, 606/48, 50; 607/2, 48, 49, 70, 72, 73; 600/16, 600/17
See application file for complete search history.

(56) References Cited

U.S. PATENT DOCUMENTS

| | | | |
|---|---|---|---|
| 5,865,787 A | 2/1999 | Shapland et al. | |
| 6,090,106 A | 7/2000 | Goble et al. | |
| 6,109,270 A | 8/2000 | Mah et al. | |
| 6,212,433 B1 | 4/2001 | Behl | |
| 6,611,706 B2 | 8/2003 | Avrahami et al. | |
| 2002/0058936 A1 | 5/2002 | Avrahami et al. | |
| 2003/0009110 A1 | 1/2003 | Tu et al. | |
| 2003/0073238 A1 | 4/2003 | Dzekunov et al. | |
| 2003/0088189 A1 | 5/2003 | Tu et al. | |
| 2004/0059389 A1 | 3/2004 | Chornenky et al. | |
| 2005/0019311 A1 | 1/2005 | Holaday et al. | |
| 2005/0043726 A1 | 2/2005 | McHale et al. | |
| 2005/0171574 A1 | 8/2005 | Rubinsky et al. | |
| 2005/0261672 A1 | 11/2005 | Deem et al. | |
| 2007/0032786 A1 | 2/2007 | Francischelli | |
| 2007/0156135 A1 | 7/2007 | Rubinsky et al. | |
| 2008/0015562 A1 | 1/2008 | Hong et al. | |
| 2008/0039746 A1 | 2/2008 | Hissong et al. | |
| 2008/0071271 A1 | 3/2008 | Francischelli | |

FOREIGN PATENT DOCUMENTS

AU    2006 202 851    7/2006
EP    1 568 395    8/2005

OTHER PUBLICATIONS

James C. Weaver, "Electroporation: A General Phenomenon for Manipulating Cells and Tissues," Journal of Cellular Biochemistry 51:426-435 (1993).
Jacob Lavee, MD, "A Novel Nonthermal Energy Source for Surgical Epicardial Atrial Ablation: Irreversible Electroporation," The Heart Surgery Forum #2006-1202; E162-E167; (Mar. 2007).

(Continued)

*Primary Examiner* — Nicholas Lucchesi
*Assistant Examiner* — Brooke Matney

(57) ABSTRACT

Cardiac electroporation ablation systems and methods in which pulsed, high voltage energy is delivered to induce electroporation of cells of cardiac tissue followed by cell rupturing. In some embodiments, the delivered energy is biphasic, having a cycle time of not more than 500 microseconds.

4 Claims, 18 Drawing Sheets

OTHER PUBLICATIONS

Jon F. Edd, "In Vivo Results of a New Focal Tssue Ablation Technique: Irreversible Electroporation," IEEE Transactions on Biomedical Engineering, vol. 53, No. 5, pp. 1409-1415; (Jun. 2006).
Liron Miller et al., "Cancer Cells Ablation with Irreversible Electroporation," Technology in Cancer Research & Treatment, vol. 4, No. 6; (Dec. 2005).
Jingsong Deng et al., "The Effects of Intense Submicrosecond Electrical Pulses on Cells," Biophysical Journal, vol. 84, pp. 2709-2714; (Apr. 2003).
D. Peter Tieleman, "The Molecular Basis of Electroporation", BioMed Central BMC Biochemistry; available at http://www.biomedcentral.com/1471-2091/5/10, pp. 1-12; (2004).
Ayman Al-Khadra et al., "The Role of Electroporation in Defibrillation," American Heart Association Circulation Research, available at http://circres.ahajournals.org/cgi/content/full/87/9/797, pp. 797-804; (2000).
Rafael V. Davalos et al., "Theoretical Analysis of the Thermal Effects During in Vivo Tissue Electroporation," Bioelectrochemistry 61, pp. 99-107; (2003).
Scott A. Freeman et al., "Theory of Electroporation of Planar Bilayer Membranes: Predictions of the Aqueous Area, Change in Capacitance, and Pore-Pore Separation," Biophysical Journal, vol. 67, pp. 42-56; (Jul. 1994).
Oscar Tovar et al., "Electroporation of Cardiac Cell Membranes with Monophasic or Biphasic Rectangular Pulses," Abstract, Pacing and Clinical Electrophysiology, vol. 14, Issue 11, 2 pgs.; (Nov. 1991).
Takashi Ashihara et al "Cell and Tssue Responses to Electric Shocks," The European Society of Cardiology, pp. S155-S165; (2005).
Xiangsheng Zheng et al., "Reduction of Atrial Defibrillation Threshold with an Interatrial Septal Electrode," American Heart Association Circulation Research, available at http://circres.ahajournals.org/cgi/content/full/102/21/2659, pp. 2659-2664; (2000).
DW Frazier et al., "Extracellular Field Required for Excitation in Three-Dimensinoal Anisotropic Canine Myocardium," American Heart Association Circulation Research, available at http://circres.ahajournals.org, pp. 147-164; (1988).
Stephan Windecker et al., "The Influence of Ventricular Fibrillation Duration on Defibrillation Efficacy Using Biphasic Waveforms in Humans," Journal of the American College of Cardiology, vol. 33, Issue 1, pp. 33-38; (Jan. 1999).
SA Feeser et al., "Strength-Duration and Probability of Success Curves for Defibrillation with Biphasic Waveforms," American Heart Association Circulation Research, available at http://circres.ahajournals.org, pp. 2128-2141; (1990).
Sunil Nath et al., "Biophysics and Pathology of Catheter Energy Delivery Systems," Progress in Cardiovascular Diseases, vol. XXXVII, No. 4, pp. 185-204; (Jan./Feb. 1995).
Tung L. Troiano GC et al., "Changes in Electroporation Thesholds of Lipid Membranes by Surfactants and Peptides," Department of Biomedical Engineering, Johns Hopkins University, pp. 249-265; (Oct. 1999).
BB Lerman et al., "Myocardial Injury and Induction of Arrhythmia by Direct Current Shock Delivered via Endocardial Catheters in Dogs," American Heart Association Circulation Research, available at http://circres.ahajournals.org, pp. 1006-1012; (1984).
Richard N.W. Hauer, MD et al., "Ventricular Tachycardia After in Vivo DC Shock Ablation in Dogs," Circulation, vol. 84, No. 1, pp. 267-278; (Jul. 1991).
Robert Lemery, MD et al., "In Vitro and in Vivo Effects Within the Coronary Sinus of Nonarcing and Arcing Shocks Using a New System of Low-Energy DC Ablation," Circulation, vol. 83, No. 1, pp. 279-293; (Jan. 1991).
R.V. Davalos et al., "Tissue Ablation with Irreversible Electroporation," Annals of Biomedical Engineering, vol. 33, No. 2, pp. 223-231; (Feb. 2005).
V.P. Nikolski et al., "Effects of Electroporation on Optically Recorded Transmembrane Potential Responses to High-Intensity Electrical Shocks," Am. J. Physiol Heart Circ. Physiol., pp. H412-H418; (Oct. 2003).
Brian J. Mossop et al., "Electric Fields Around and Within Single Cells During Electroporation—A Model Study," Annals of Biomedical Engineering; (2007).
O. Tovar et al., "Electroporation and Recovery of Cardiac Cell Membrane with Rectangular Voltage Pulses," AJP Heart and Circulatory Physiology, vol. 263, Issue 4; 3 pgs; (1992).
T.R. Gowrishankar et al., "Electrical Behavior and Pore Accumulation in a Multicellular Model for Conventional and Supra-Electroporation," Biochemical and Biophysical Research Communications 349, pp. 643-653; (2006).
Vladimir P. Nikolski et al., "Electroporation of the Hearth," European Society of Cardiology, pp. S146-S154; (2005).
Mark M. Gallagher et al., Embolic Complications of Direct Current Cardioversion of Atrial Arrhythmias: Journal of the American College of Cardiology, vol. 40, Issue 5, pp. 926-933; (Sep. 2002).
Katsuhiro Ohuchi et al., "A Dynamic Action Potential Model Analysis of Shock-Induced Aftereffects in Ventricular Muscle by Reversible Breakdown of Cell Membrane," IEEE Transactions on Biomedical Engineering, vol. 49, No. 1, pp. 18-30; (Jan. 2002).
Antoni Ivorra et al., "In Vivo Electrical Impedance Measurements During and After Electroporation of Rat Liver," Bioelectrochemistry 70, pp. 287-295; (2006).
Julie Gehl et al., "In Vivo Electroporation of Skeletal Muscle: Threshold, Efficacy and Relation to Electric Field Distribution," Biochimica et Biophysica Acta 1428, pp. 233-240; (1999).
Mark M. Gallagher et al., "Initial Energy Setting, Outcome and Efficiency in Direct Current Cardioversion of Atrial Fibrillation and Flutter," Journal of the American College of Cardiology, vol. 38, Issue 5, pp. 1498-1504; (Nov. 2001).
Alenka Macek Lebar et al., "Inter-Pulse Interval Between Rectangular Voltage Pulses Affects Electroporation Threshold of Artificial Lipid Bilayers," IEEE Transactions on Nanobioscience, vol. 1, No. 3, pp. 116-120; (Sep. 2002).
Uwe F. Pliquett et al., "Kinetics of the Temperature Rise within Human Stratum Corneum During Electroporation and Pulsed High-Voltage Iontophoresis," Bioelectrochemistry 57, pp. 65-72; (2002).
MM Scheinman et al., "Catheter Ablation of the Atrioventricular Junction: A Report of the Percutaneous Mapping and Ablation Registry," American Heart Association Circulation Research, available at http://circres.ahajournals.org, pp. 1024-1029; (1984).
MM Scheinman et al., "Catheter Ablation for Treatment of Tachyarrhythmias: Present Role and Potential Promise," American Heart Association Circulation Research, available at http://circres.ahajournals.org, pp. 10-13; (1986).
N.J. Rowan et al., "Pulsed Electric Field Inactivation of Diarrhoeagenic *Bacillus cereus* Through Irreversible Electroporation," Letters in Applied Microbiology, pp. 110-114; (2000).
G. Thomas Evans, Jr., MD et al., "Predictors of In-Hospital Mortality After DC Catheter Ablation of Atrioventricular Junction," Circulation 84, pp. 1924-1937; (1991).
Molly Weaver et al., "Powerful Ideas Driven by Simple Tools: Lessons from Experimental Embryology," Nature Cell Biology, vol. 3; (Jul. 2001).
David Ker-Liang Cheng et al., "Nonuniform Responses of Transmembrane Potential During Electric Field Stimulation of Single Cardiac Cells," American Physiological Society, pp. H351-H362; (1999).
R. Lemery et al., "Success, Safety, and Late Electrophysiological Outcome of Low-Energy Direct-Current Ablation in Patients with the Wolff-Parkinson-White Syndrome," American Heart Association Circulation Research, available at http://circres.ahajournals.org, pp. 957-962; (1992).
I.P. Sugar et al., "Stochastic Model for Electric Field-Induced Membrane Pores Electroporation," Biophysical Chemistry, vol. 19, Issue 3, Abstract (2 pgs.); (May 1984).
Zlatko Vasilkoski et al., "Membrane Electroporation: The Absolute Rate Equation and Nanosecond Time Scale Pore Creation," Phys. Rev. E. 74, 12 pgs.; (2006).
RP Joshi et al., "Self-Consistent Simulations of Electroporation Dynamics in Biological Cells Subject to Pulses," The American Physical Society, Issue 1; 10 pgs.; (Jun. 2001).
Joseph P. Allegretti MD et al., "Electroporation Therapy for Head and Neck Cancer Including Carotid Artery Involvement," The American Laryngological, Rhinological & Otalogical Society, Inc., vol. 111(1), pp. 52-56; (Jan. 2001).
I. Perez-Molina et al., "Neurological Sequelae Following Electrocution. A Case Report and Review of the Literature," Rev. Neurol. 43; 2 pgs.; (Nov. 2006).
Wanda Krassowska et al., "Modeling Electroporation in a Single Cell," Biophys J. BioFAST 92, 1 pg.; (2007).

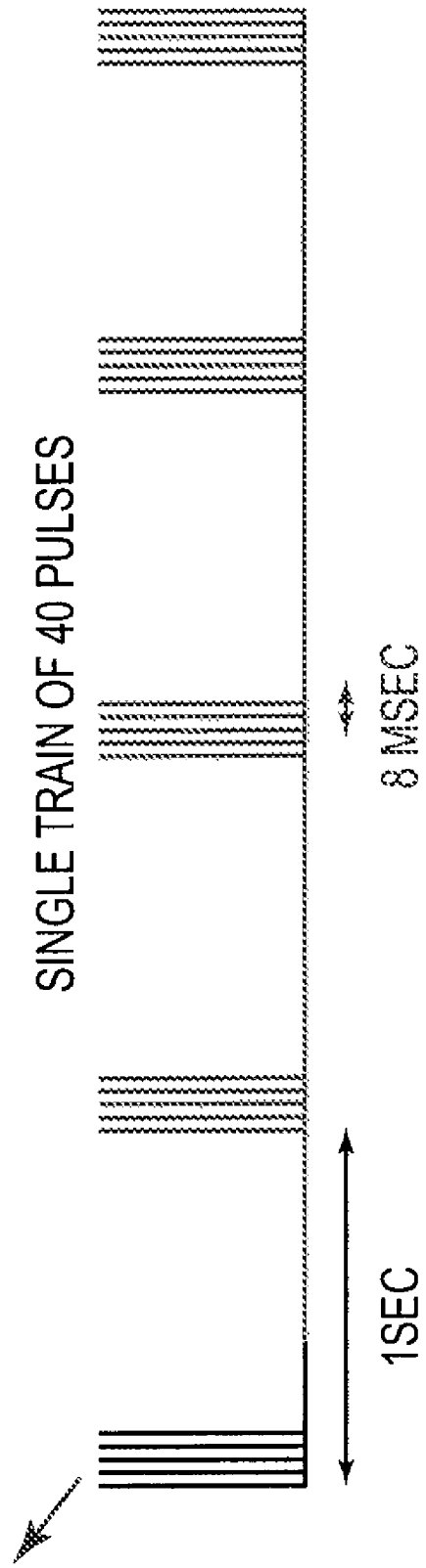

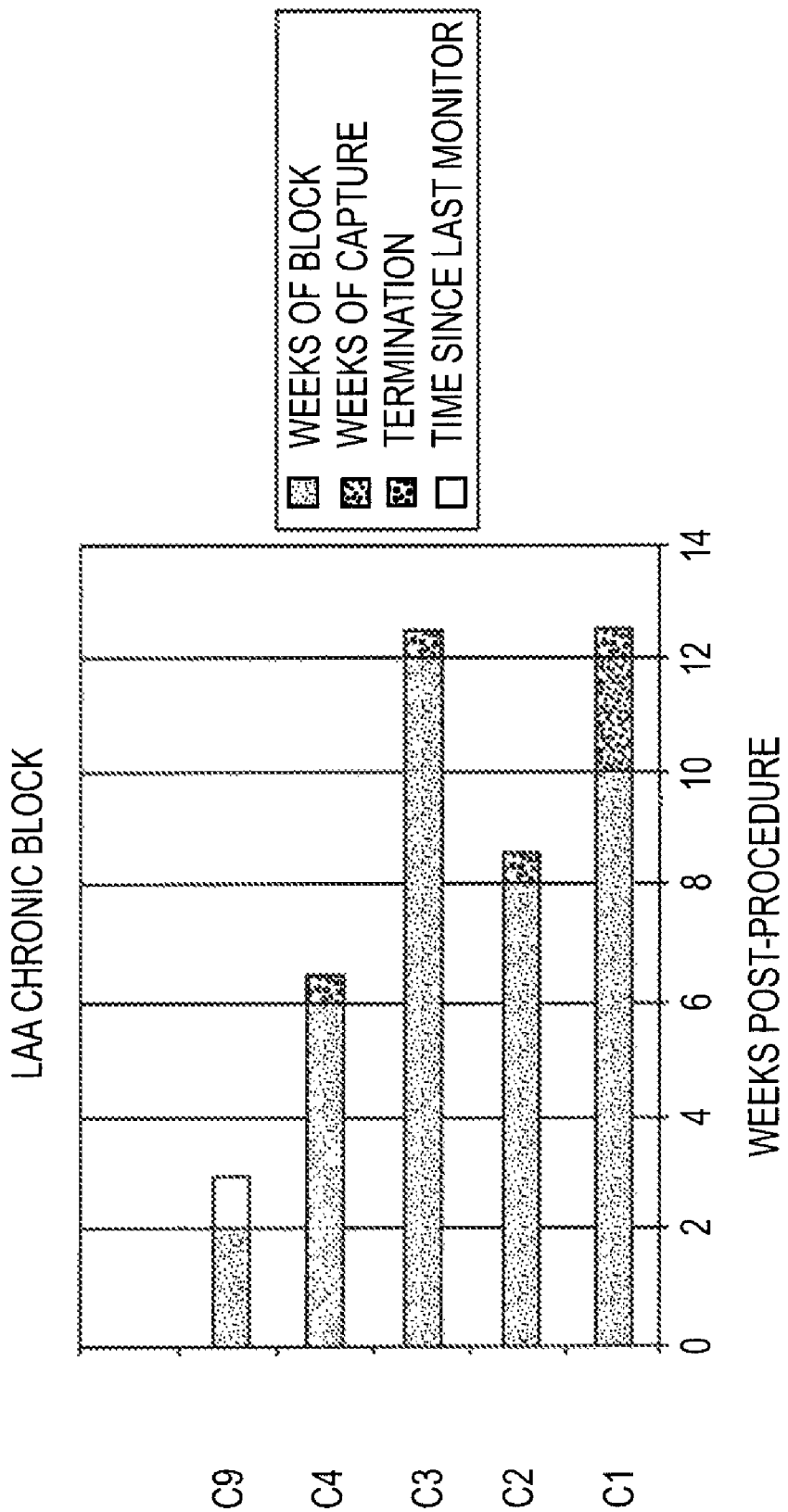

SYSTEMS AND METHODS FOR CARDIAC TISSUE ELECTROPORATION ABLATION

CROSS-REFERENCE TO RELATED APPLICATION

This application claims priority under 35 U.S.C. §119(e)(1) to U.S. Provisional Patent Application Ser. No. 61/084,149, filed Jul. 28, 2008, entitled "Systems and Methods for Cardiac Tissue Electroporation Ablation", and bearing the entire teachings of which are incorporated herein by reference.

BACKGROUND

The present disclosure relates generally to the treatment of cardiac tissue of a patient with ablative energy. More particularly, it relates to ablation of cardiac tissue using high voltage ablation, for example via high voltage electroporation ablation or irreversible electroporation (IEP) ablation.

There are many medical treatments that involve instances of cutting, ablating, coagulating, destroying, or otherwise changing the physiological properties of tissue. These techniques can be used beneficially to change the electrophysiological properties of tissue, for example by ablation of cardiac tissue to cure various cardiac conditions. As a point of reference, normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node (or "AV node") and the bundle of HIS (or "HIS bundle") to myocardial tissue cells of the ventricles. The depolarization of cells propagates across the ventricles, causing the ventricles to contract. This conduction system results in the described, organized sequence of myocardial contraction leading to a normal heartbeat.

Sometimes, aberrant conductive pathways develop in heart tissue, which disrupts the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles. Additionally, it has been hypothesized that multiple microeentrant wavelets can occur in myocardium that has remodeled, such that it can more easily sustain fibrillatory conduction patterns such as in atrial fibrillation. In such atrial myocardium, there may be a dispersion of atrial refractoriness, whereby there is variation in the effective refractory period over the atrial wall. When such tissue is exposed to rapid conduction wavefronts or asynchronus ectopic focal triggers, a portion of those myocardial cells are still in a refractory state. This leads to the circulating chaotic wavefronts that are known collectively as atrial fibrillation (AF). Curative ablation therapies for AF focus on creation of linear lesions that compartmentalize the atria and direct conduction along selected pathways that are intended to promote organized conduction while isolating AF triggers from connecting with the atria.

The aberrant conductive pathways create abnormal, irregular, and sometimes life-threatening heart rhythms called arrhythmias. An arrhythmia can take place in the atria, for example, as in atrial tachycardia, atrial fibrillation, or atrial flutter. The arrhythmia can also take place in the ventricle, for example, as in ventricular tachycardia.

As indicated above, surgical procedures can be performed to treat heart arrhythmias, and in particular via formation of one or more lesions that interrupt the conduction routes of the most common reentry circuits. For example, a surgical procedure called the "Maze" procedure (and variations of the Maze procedure) was designed to eliminate atrial fibrillation permanently. The procedure employs incisions in the right and left atria which divide the atria into electrically isolated portions that in turn results in an orderly passage of the depolarization wave front from the SA node to the AV node while preventing reentrant wave front propagation.

The lesions formed in connection with the Maze procedure, as well as other cardiac tissue applications, can be imparted via ablation. Conventionally, cardiac tissue ablation is effectuated by placement of one or more ablating members (e.g., electrodes), and applying energy at certain levels to achieve the desired result of killing of cells at the ablation site while leaving the basic structure of the organ to be ablated in tact. RF energy has been found to be highly viable in this regard, and is commonly employed. Other ablative techniques include ultrasound, microwave, laser, cytotoxic agents, etc. In certain instances, conventional cardiac tissue ablation systems may not achieve optimal results in terms of complete transmural ablation (e.g., ablation lesion extending through a thickness of the ablated tissue structure) with minimal, if any, impact on surrounding tissue. For example, excessive thermal conditions may be a concern with RF ablation. Thus, any improvements in cardiac tissue ablation systems and methods that limit hyperthermy will be well-received.

SUMMARY

Some aspects in accordance with principles of the present disclosure relate to a method of performing an electroporation ablation procedure on tissue of a patient. At least one electrode is positioned on the tissue, and pulsed, high voltage biphasic energy is delivered to the electrode to induce electroporation of cells of the tissue followed by cell rupturing. In some applications, the pulsed, biphasic energy has a cycle time of not more than 500 microseconds, and is delivered at an output voltage in the range of 200-700 volts and a pulse width in the range of 50-200 microseconds. In other embodiments, the electroporation ablation procedure is performed on heart tissue.

Other aspects in accordance with principles of the present disclosure relate to a cardiac tissue electroporation ablation system including a delivery instrument and an electrical pulse generator. The delivery instrument maintains at least one electroporation electrode, and the pulse generator is electrically connected to the electroporation electrode. In this regard, the pulsed generator is programmed to deliver pulsed, high voltage energy to the electroporation electrode sufficient to induce IEP ablation of cardiac tissue cells, including an output voltage in the range of 200-700 volts, a pulse width in the range of 50-200 microseconds, a pulse interval in the range of 100-400 microseconds, and as a series of pulse trains over a range of 2-6 seconds with a train interval in the range of 200-1,000 milliseconds. In some embodiments, the pulse generator is further programmed to deliver the pulsed, high voltage energy as biphasic pulses. In other embodiments, the electroporation electrode is formed of a metal material constructed to release cytotoxic metal ions in the presence of pulsed energy.

BRIEF DESCRIPTION OF THE DRAWINGS

FIG. 3 is an example pulse train series useful in electroporation ablation of cardiac tissue in accordance with principles of the present disclosure;

FIG. 14 is a plot of conduction block evaluations of chronic heart samples subjected to left atrial appendage electroporation ablation in connection with an in vivo study.

DETAILED DESCRIPTION

The cardiac tissue ablation systems and methods of the present disclosure generally provide or rely upon electroporation. "Electroporation" utilizes high voltage, short (e.g., microsecond to millisecond) electrical pulses to effectuate a physiological modification (i.e., permeabilization) of cell membranes to which the energy is applied. In particular, the pulsed energy induces the formation of microscopic pores or openings in the cell membrane. Depending upon the characteristics of the electrical pulses, an electroporated cell can survive electroporation (i.e., "reversible electroporation") or die (i.e., IEP). As used herein, IEP is a biological ablation technique that creates pores in the cell membrane. Conventionally, reversible electroporation has been used to transfer agents into targeted cells for various purposes. Irreversible electroporation has previously been considered for ablation of liver tissue, and benign or malignant tumors.

Figure 1:
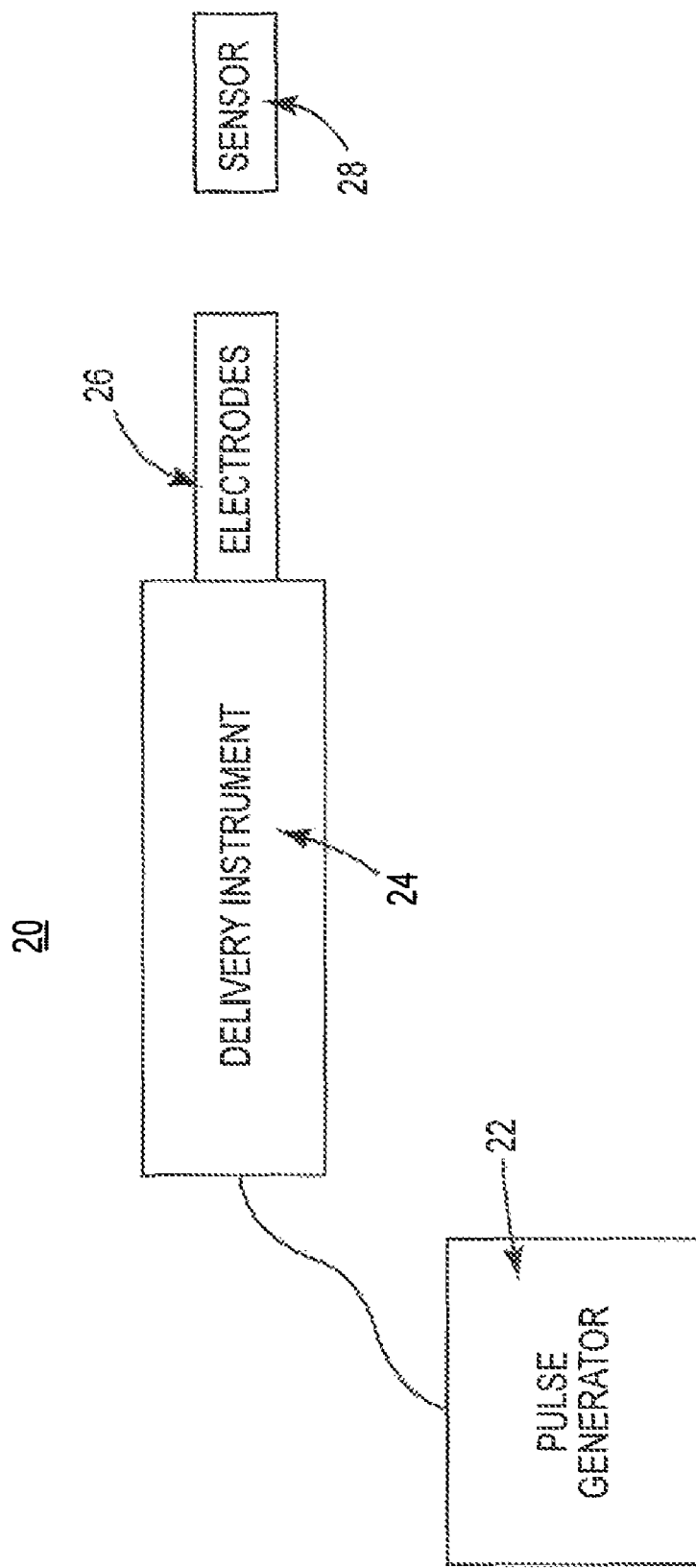
FIG. 1 is a block diagram of a cardiac tissue electroporation ablation system in accordance with principles of the present disclosure and useful in performing methods of the present disclosure.

With the above in mind, one embodiment of a cardiac tissue electroporation ablation system 20 is shown in block form in FIG. 1. In general terms, the system 20 includes a pulse generator 22, a delivery instrument 24, and one or more electroporation electrodes 26. Optionally, one or more sensors 28 (e.g., mapping electrodes) can also be carried by the delivery instrument 24. The electroporation electrodes 26 are electrically connected to the pulse generator 22 via the delivery instrument 24. Further, the delivery instrument 24 is sized and shaped for facilitating surgeon-controlled arrangement of the electroporation electrodes 26 at a desired cardiac tissue site. In this regard, the delivery instrument 24, as well as the electroporation electrodes 26 carried thereby, can assume a wide variety of forms appropriate for a particular surgical procedure, including open chest, minimally invasive, etc. Thus, the delivery instrument 24 can be a clamp-like device, a pen-like handle, catheter-based, etc. Regardless, the pulse generator 22 is configured and programmed to deliver pulsed, high voltage density energy as described below, appropriate for achieving desired pulsed, high voltage ablation (or IEP ablation). As a point of reference, the pulsed, high voltage ablation effects of the present disclosure are distinguishable from DC current ablation, as well as thermally-induced ablation attendant with conventional RF techniques. The IEP in accordance with the present disclosure is sufficient to induce cell death for purposes of completely blocking an aberrant conductive pathway along or through cardiac tissue, destroying the ability of the so-ablated cardiac tissue to propagate or conduct an electrical signal.

In some embodiments, the pulse generator 22 is capable of delivering a number of different various waveforms or shapes of pulses to achieve electroporation ablation of cardiac tissue, including sinusoidal AC pulses, DC pulses, square wave pulses, exponentially decaying waveforms, or other pulse shapes such as combined AC/DC pulses, or DC shifted signals such as those described by Chang in *Cell Poration and Cell Fusion Using an Oscillating Electric Field*, Biophysical Journal, October 1989, Volume 56, pp. 641-652, depending upon the pulse generator 22 used and/or the effect desired. The parameters of pulsed energy generated by the pulse generator 22 can vary in one or more of the following manners: waveform shape, pulse polarity, amplitude, pulse duration, interval between pulses, number of pulses per second (frequency), total number of pulses, combination of waveforms, etc. One or more of these parameters can be altered or changed during the ablation procedure. In more general terms, the pulse generator 22 is adapted to generate a high density energy gradient in the range of 10-1,000 V/cm, pulsed at rates on the order of 1-1,000 microseconds. The voltage level, pulse rate, waveform, and other parameters can be varied as described below, with the pulse generator 22 including, in some embodiments, a controller that automatically dictates operational parameters as a function of one or more characteristics of the cardiac tissue target site (e.g., tissue type (such as fatty tissue, thickness, cell orientation, naturally-occurring electrical activity, etc.)).

Figure 2A:
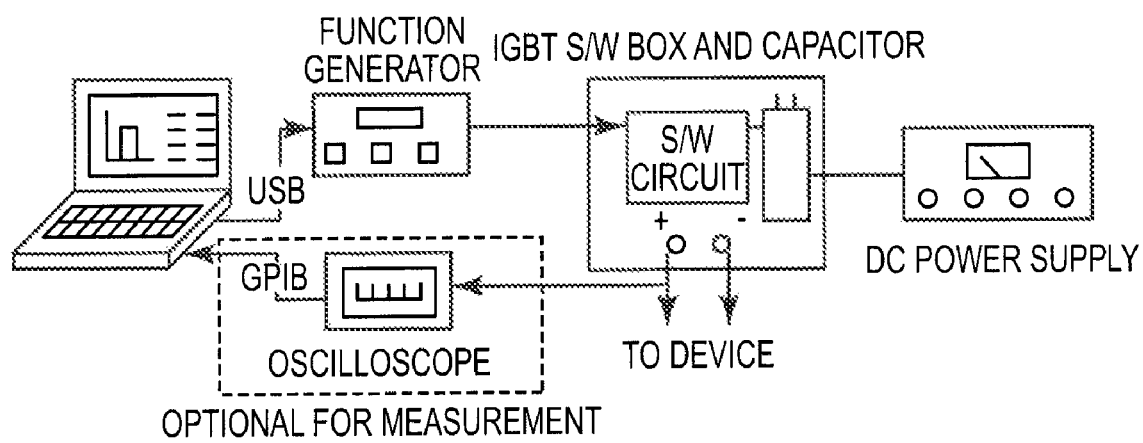
FIG. 2A is a schematic illustration of a pulse generator useful with the electroporation ablation system of FIG. 1.
Figure 2B:
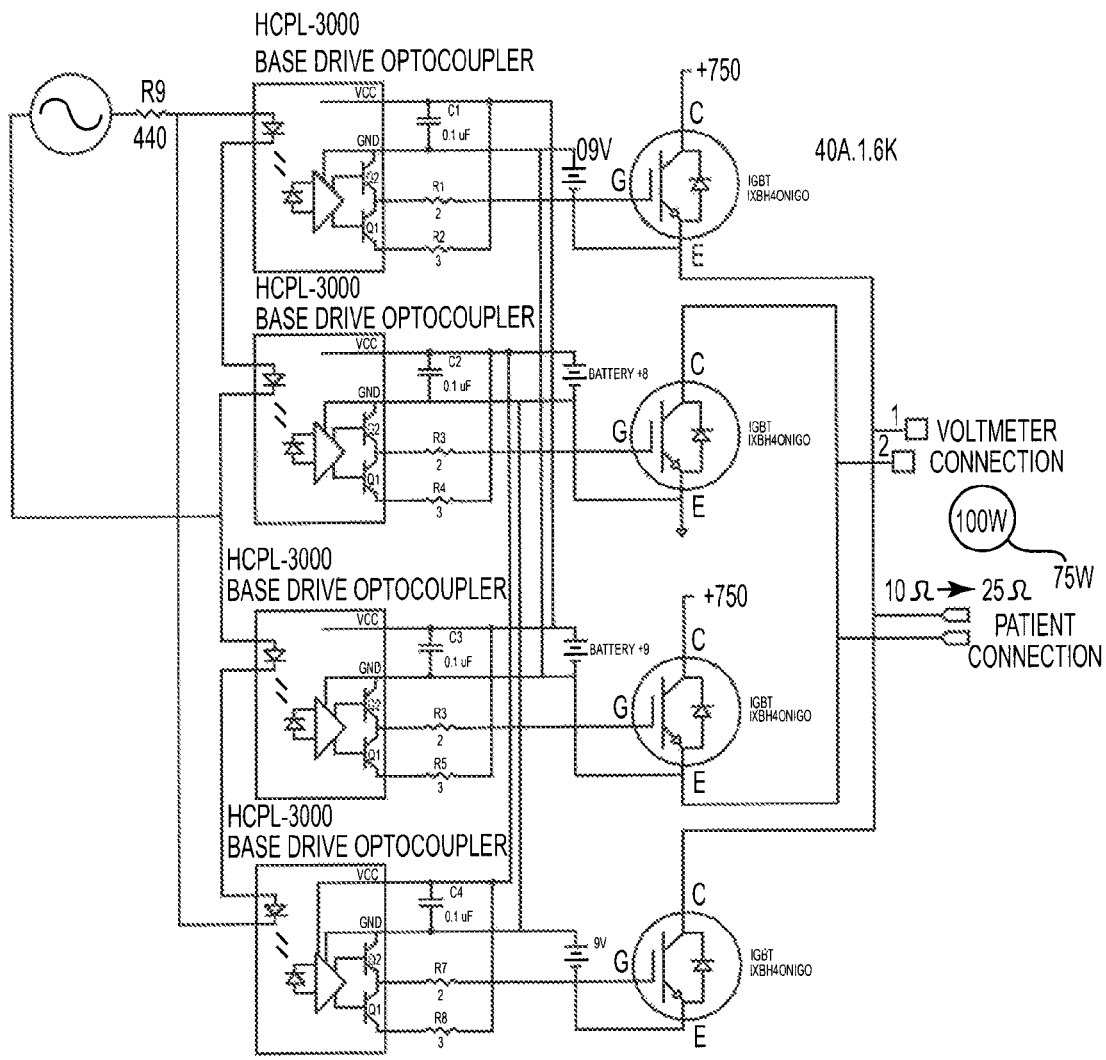
FIG. 2B is a circuit diagram of a switching circuit useful with the pulse generator of FIG. 2A.

In order to deliver effective electroporation ablation energy, the pulse generator 22 should be adapted to reliably deliver high voltage. With this in mind, the pulse generator 22 can be provided in a form akin to defibrillator voltage generators, such as a defibrillator generators available from Medtronic, Inc. (e.g., LIFEPAK 20 defibrillator system). In this regard, the pulse generator 22 can include or be controlled by a controller/software (e.g., LabVIEW software) that permits user selection of various pulse parameters such as pulse width, interval, number of pulses, and burst frequency. FIG. 2A schematically illustrates an alternative pulse generator 22' construction in which a function generator 30 (e.g., an Agilent Model 3320 function generator) serves to trigger operation of an insulated gate bipolar transistor (IGBT) switching circuitry 32 via independent optocouplers that isolate high voltage from a high energy capacitor. One construction of the switching circuitry 32 is provided in FIG. 2B. Returning to FIG. 2A, a controller 34 (e.g., a computer loaded with Lab VIEW software) permits selection of burst pulses in various frequencies on the function generator 30. With this construction, the pulse generator 22' is capable of delivering a wide range of burst pulses (e.g., minimum pulse width of 1 μs and inter-pulse interval of 10 μs both in monophasic and biphasic modes).

Returning to FIG. 1, in some embodiments, the system 20 is configured such that the pulse generator 22 delivers biphasic electrical pulses to the electroporation electrodes 26. As a point of reference, while monophasic electrical pulses may alternatively be employed, the application of biphasic electrical pulses has surprisingly been found to produce unexpectedly beneficial results in the context of cardiac tissue ablation. With biphasic electroporation pulses, the direction of the pulses completing one cycle alternates in less than a few hundred microseconds. As a result, the cells to which the biphasic electrical pulses are applied undergo alternation of electrical field bias. With IEP cardiac tissue ablation, changing the direction of bias surprisingly helps to reduce prolonged post-ablation depolarization and/or ion charging. As a result, it reduces prolonged muscle excitation (e.g., skeletal and cardiac cells) and risks of post shock fibrillation of the cardiac cells. Further, biphasic electrical pulses (alternating current) have been surprisingly found to overcome the high impedance characteristics of fatty cells often times associated with cardiac ablation procedures. Thus, biphasic electrical pulses have been found to surprisingly avoid the possible drawbacks of monophasic electrical pulses including: 1) atrial or ventricular fibrillation, 2) less effective in making lesions through fat, 3) propensity to make thermal lesions on the anode side of an electrode pair, and 4) prolonged muscle excitation.

Figure 4:
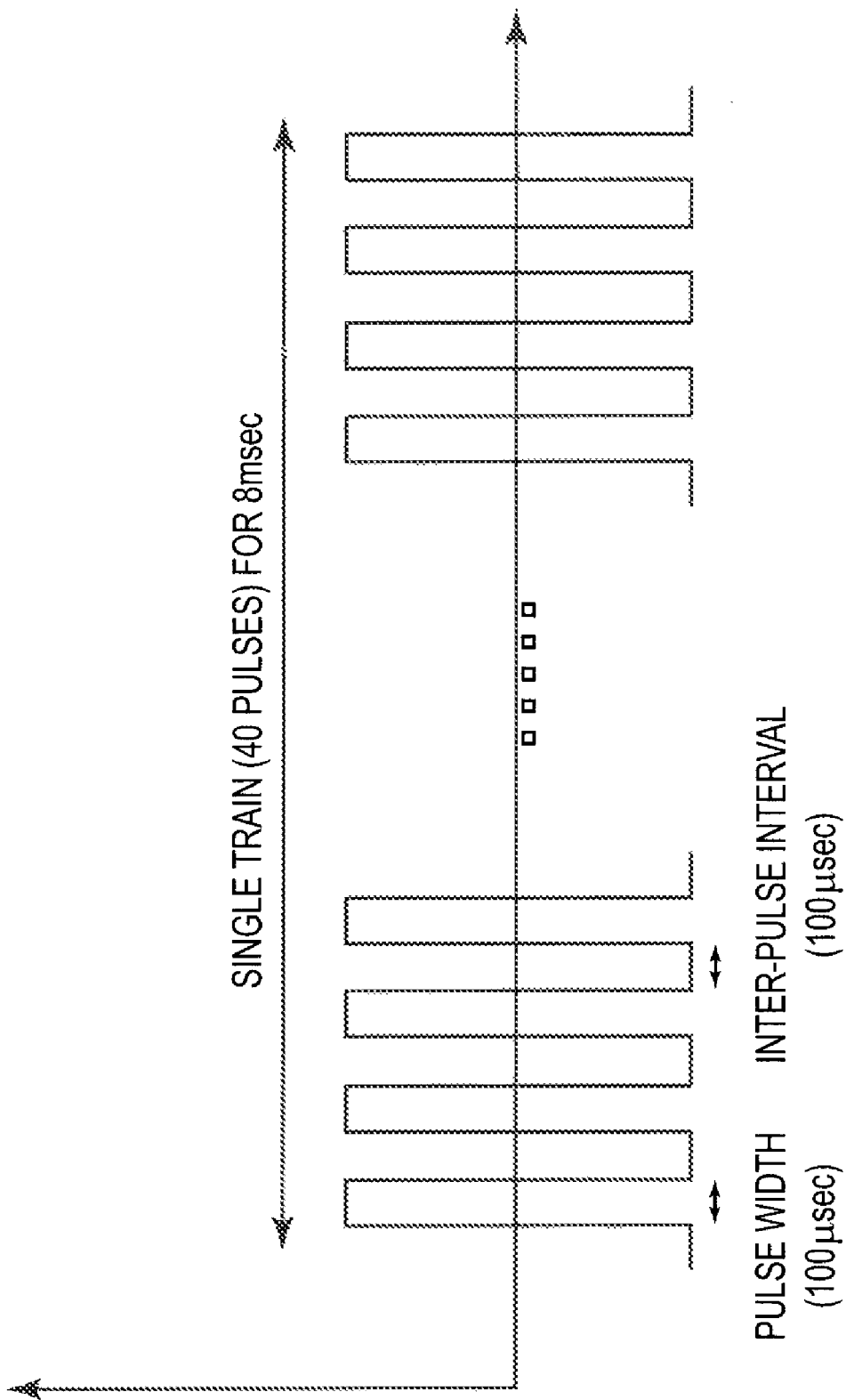
FIG. 4 is an enlarged representation of one of the biphasic pulse trains of FIG. 3.
Figure 5A:
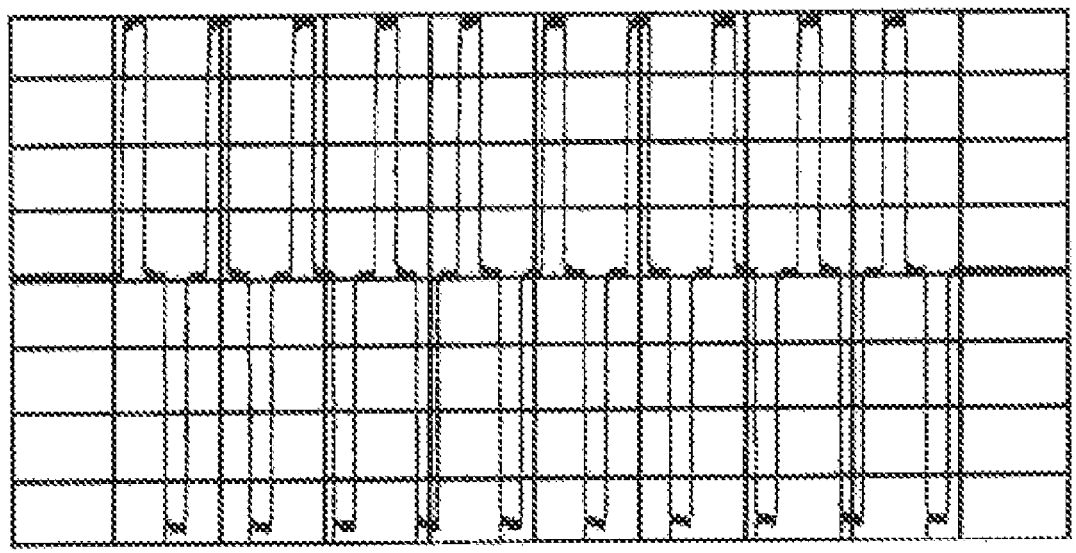
FIGS. 5A-5E are example waveforms of pulsed, high voltage IEP energy in accordance with principles of the present disclosure.
Figure 5B:
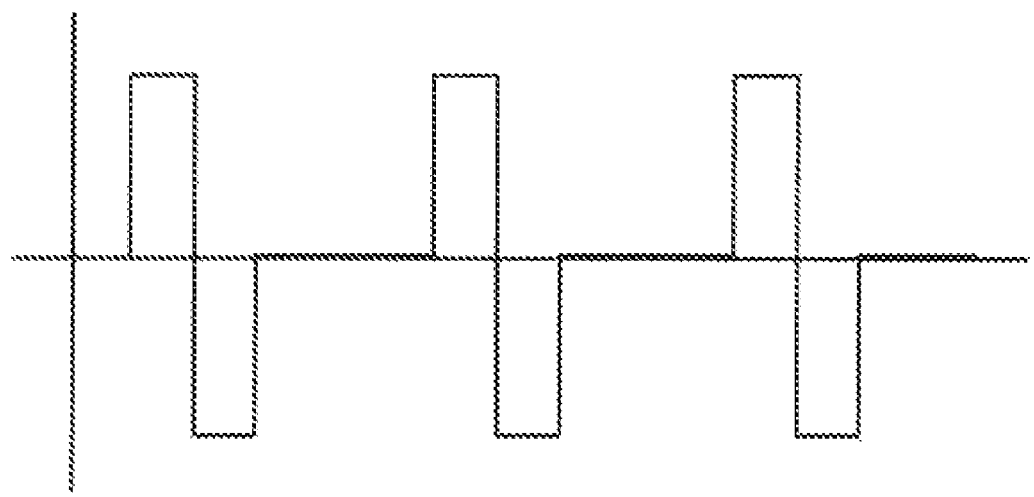
Figure 5C:
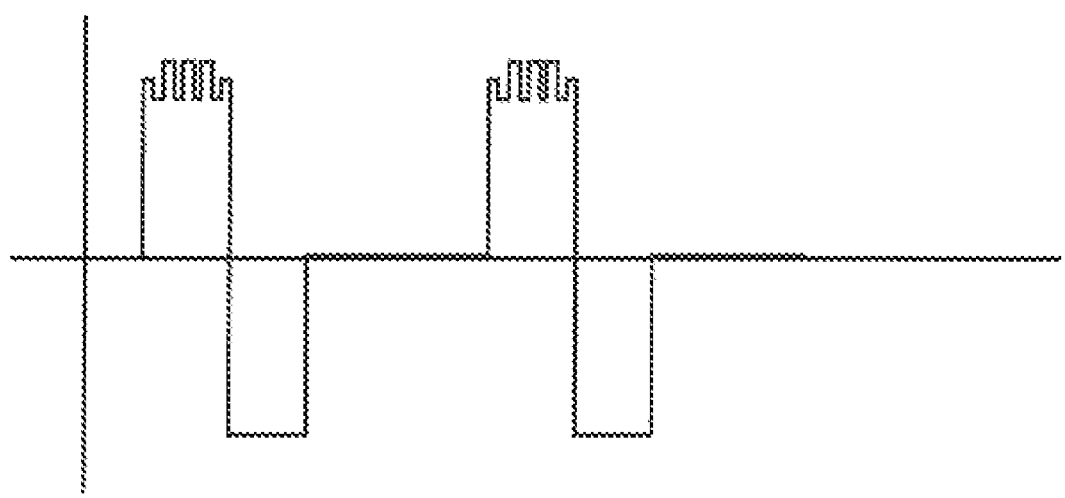
Figure 5D:
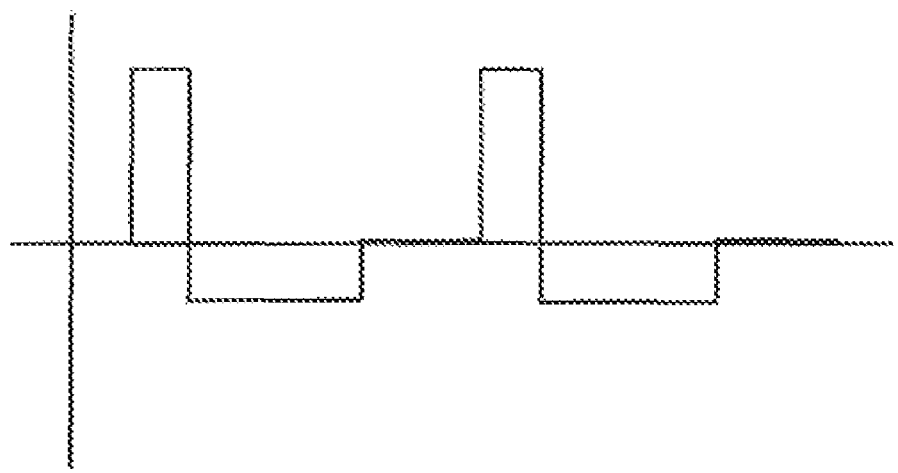
Figure 5E:
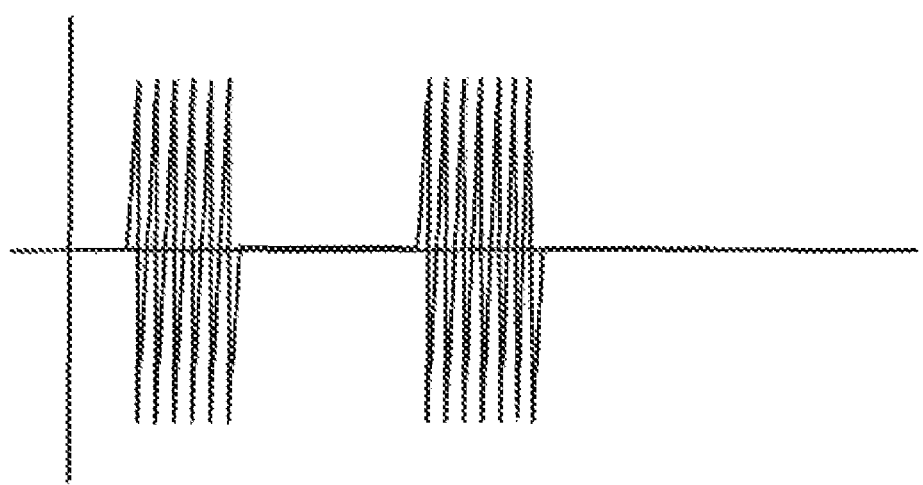

With respect to biphasic energy, in some embodiments, the pulse generator 22 is programmed to deliver a series (e.g., 1 to 6) of pulse trains for 2-6 seconds at frequencies on the order of 1 Hz (i.e., a one second burst of energy). Each train can consist of 10 to 60 biphasic (i.e., half positive phase and half negative phase) pulses. With these applications, an output voltage from the pulse generator 22 is in the range of 200-700 volts at currents in the range of 8-25 Amps. With some constructions of the delivery instrument 24 and the electrodes 26 in which a bipolar clamping device is provided, this output voltage levels (300-700 volts) provides a voltage intensity on the order of 1,500-2,500 V/cm across 2 mm thick tissue. With this in mind, FIG. 3 illustrates an exemplary string 50 of biphasic pulses in accordance with principles of the present disclosure for effectuating transmural ablation of cardiac tissue by IEP delivered over 5 seconds, with each train or train segment 52 comprised of 40 pulses over 8 milliseconds at a frequency of 1 Hz. FIG. 4 illustrates one of the exemplary pulse trains 52 in greater detail, having a biphasic pulse width and inter-pulse interval of 100 microseconds. Other biphasic waveforms can also be employed, having differing parameters such as shapes, amplitudes, pulse duration, interval between pulses, combination of pulses, etc. In general terms, in some embodiments, biphasic energy pulses applied at very short durations (on the order of 1 nanosecond-50 microseconds, up to 100 microseconds, in some embodiments in the range of 50-200 microseconds) are effective in ablating through fatty areas of heart tissue. Further, trains of short biphasic pulses having low amplitude can be effective in permeablized cells and still minimize thermal damage. In some embodiments, the delivered biphasic pulse trains are provided over a range of 2-6 seconds at 1-5 Hz, each train having 20-60 biphasic pulses, 5-200 microseconds in width, at 100-400 microsecond pulse intervals and 250-1,000 millisecond train intervals, in a range of 300-500 volts.

As indicated above, a waveform of the pulsed, high voltage energy as generated by the pulse generator 22 can have a variety of formats. Several non-limiting examples of waveforms in accordance with the present disclosure are shown in FIGS. 5A-5E.

In addition to the parameters of the delivered, pulsed energy, in some embodiments, the system 20 and related cardiac ablation methods are adapted to correlate delivery of energy with the natural or paced depolarization-repolarization cycle of the cardiac muscle in a beating heart. For example and returning to FIG. 1, the system 20 can be configured to include the optional sensor 28 as an electrode(s) capable of sensing electrical activity propagating along cardiac tissue; alternatively a separate electrical sensing component apart from the delivery instrument 24 can be employed. Regardless, the pulse generator 22 includes, or is electrically connected to, a controller that interprets the sensed electrical activity, and based upon this interpretation, dictates and/or adjusts timing of the delivery of the pulsed electroporation-causing energy.

The sensed, naturally-occurring electrical activity can be provided in the series of waveforms observed on an electrocardiogram (ECG) recording. As a point of reference, a typical ECG tracing of a normal heartbeat (or cardiac cycle) consists of a P wave, a QRS wave complex, and a T wave. During normal atrial depolarization, the main electrical vector is directed from the SA node towards the AV node and spreads from the right atrium to the left atrium. This correlates with the P wave on the ECG. The QRS wave complex is a representation on the ECG that corresponds with the depolarization of the ventricles. Because the ventricles contain more muscle mass than the atria, the QRS wave complex is larger than the P wave. Finally, the T wave represents the repolarization (or recovery) of the ventricles. In other words, the QRS wave complex is an indication that the cardiac myocytes in the ventricles have depolarized, causing contraction of the heart. The T wave is an indication that the ventricular cardiac myocytes have repolarized and are prepared to repeat the depolarization observed again as a QRS wave complex.

Figure 6:
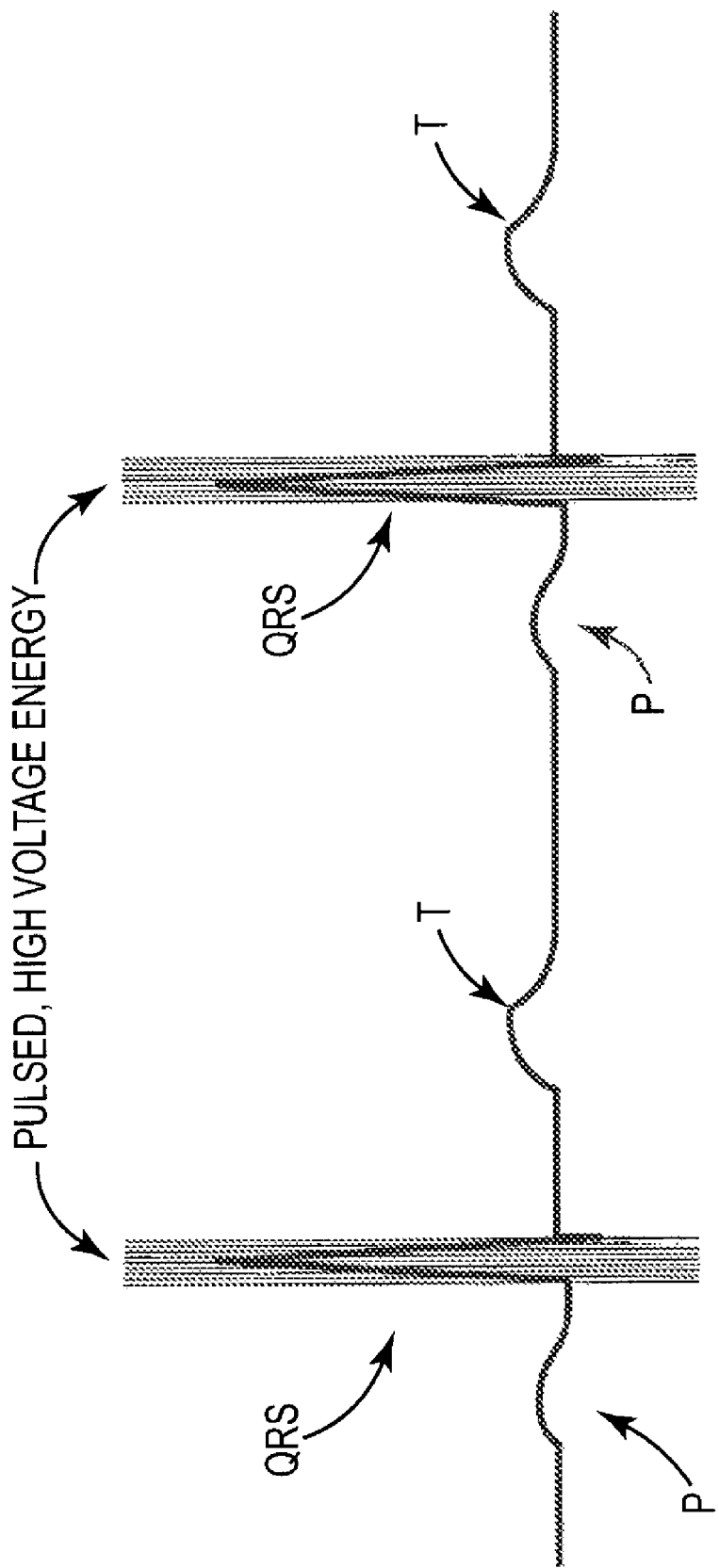
FIG. 6 illustrates application of high voltage, pulsed energy as a function of a sensed ECG trace in performing cardiac tissue electroporation ablation in accordance with the present disclosure.

Given the above, in some embodiments, the system 20 is adapted (e.g., the controller program) to time the delivery of high voltage, pulsed energy as a function of the sensed cardiac cycle to which the delivery of pulsed, high voltage energy is guided. In either case, the determined timing is a function not only of the sensed/paced cardiac cycle, but also of the cardiac tissue to be ablated. For example, with ventricular cardiac tissue, the present disclosure contemplates the high density energy pulses (as described above) being applied during the QRS wave complex or segment. During the QRS wave complex, the ventricular cells are actively pumping ions through the cell membranes to effect depolarization. By timing the pulsed, electroporation energy with this period, the high voltage energy is applied when the local cellular lethal threshold for high voltage pulses is reduced. This, in turn, allows more efficient use of the applied high voltage to cause cell death and local conduction block. Notably, with embodiments in which the delivery of pulsed, high voltage is tailored as a function of heart rate, frequencies of less than 1 Hz are beneficial. With this in mind, FIG. 6 illustrates timed or gated delivery of electroporation energy pulses to ventricular tissue as a function of a sensed (or paced) ECG trace.

The time or gated delivery of high voltage, pulsed energy can assume a different format where the tissue to be ablated is atrial tissue. More particularly, the pulsed, high voltage energy can be optimized in ablation of atrial myocardium, using the P wave portion of the ECG recording as the gating reference point in the cardiac cycle. The atrial myocardium cells exhibit a reduced threshold for high voltage pulses when depolarizing; by timing the delivery or gating of pulsed, high voltage energy to correspond with the P wave segment, enhanced cardiac ablation or atrial tissue is promoted with lower output voltage gradients.

Returning to FIG. 1, the gated or timed delivery of electroporation energy as a function of natural and/or paced electrical activity described above is useful with any of the embodiments of the present disclosure. Thus, for example, biphasic or monophasic energy can be employed. Similarly, the gated delivery approach can be implemented with a wide range of delivery instrument 24 and/or electroporation electrode 26 designs.

In addition or as an alternative to automatically controlling the delivery of the short, high voltage electrical pulses as a function of the natural and/or paced polarization-repolarization of the cardiac myocytes, in other embodiments, the system 20 can control one or more parameters of the delivered energy as a function of other sensed characteristics. For example, in some embodiments, the pulse generator 22 includes, or is connected to, a controller that is programmed to control the energy delivery as a function of sensed impedance (via, for example, the optional sensor(s) 28). More particularly, prior to the delivery of the pulsed, high voltage energy, a short, low energy pulse is delivered to the cardiac tissue to measure a base line impedance value. This value is then used for determining optimal parameters of the subsequently delivered, high voltage energy as described below.

As a point of reference, optimization of the electroporation pulsed energy is, at least in part, a function of a thickness and composition of a tissue to be ablated (where a transmural lesion is desired). Optimal energy parameters (e.g., voltage, pulse duration, etc.) are characterized as those resulting in a narrow, transmural lesion, with minimal damage to surrounding tissue and not generating excessive heat (or tissue "pops"). Thus, a thickness of the tissue to be ablated directly affects the optimal energy parameters, and can be estimated, for example, based upon the measured impedance. With this in mind, by measuring tissue impedance in response to a low voltage test energy pulse, tissue thickness can be evaluated, and then employed to determine the optimal energy level sufficient to induce electroporation of cells followed by cell rupturing with minimal damage to surrounding tissue. In other embodiments, the tissue impedance is periodically or continuously measured throughout the ablation procedure, with the system 20 being configured to alter the energy parameters as a function of changing impedance measurements. For example, where the impedance is determined to be increasing, one or more of the voltage, number of pulses, pulse width, etc., can be automatically reduced.

In addition or as an alternative to impedance, other target site tissue characteristics can be measured or sensed (e.g., via the optional sensor(s) 28) and used as a basis for automatically selecting and/or controlling the delivered, high voltage energy pulses. For example, tissue pH can be measured. In this regard, it has been postulated that with tissue ablation, hydrogen ions are created, that in turn alter the tissue pH. Where an excessive change in pH is sensed outside the range of normal physiological pH (e.g., acid or basic) the system 20 (i.e., a controller provided with or electrically connected to, the pulse generator 22) can be adapted or programmed to interpret this change as an indication that the voltage of the applied, pulsed energy is too high and should be reduced.

In addition or as an alternative to providing a baseline value upon which the pulsed energy parameter(s) can be controlled during a cardiac tissue electroporation ablation procedure, impedance measurements can be employed to evaluate a directionality of the tissue/cells to be ablated. Other techniques (including a visual confirmation) can alternatively be employed in making this evaluation. Regardless, tissue/cell directionality is another, optional characteristic of the ablation target site upon which electroporation procedures in accordance with the present disclosure can be based. For example, where the electroporation electrodes 26 are linear electrodes (i.e., length greater than width), the electrodes 26 are optimally arranged "in line" with the evaluated directionality of the tissue/cells to be ablated, thereby reducing the voltage gradient necessary for achieving a transmural lesion. Cardiac myocytes are such elongated cells that are typically arranged with the long axis of the muscle cells aligned with each other. When a voltage is applied transverse to the long axis of the cells, the voltage gradient per cell is less than the gradient per cell when the voltage is applied in line with the long axis of the muscle cells. The higher the intracellular voltage gradient, the more likely that irreversible electroporation will occur. Thus, alignment of the applied electric field with muscle fiber orientation can be used to reduce the required voltage to effect electroporation.

Figure 7:
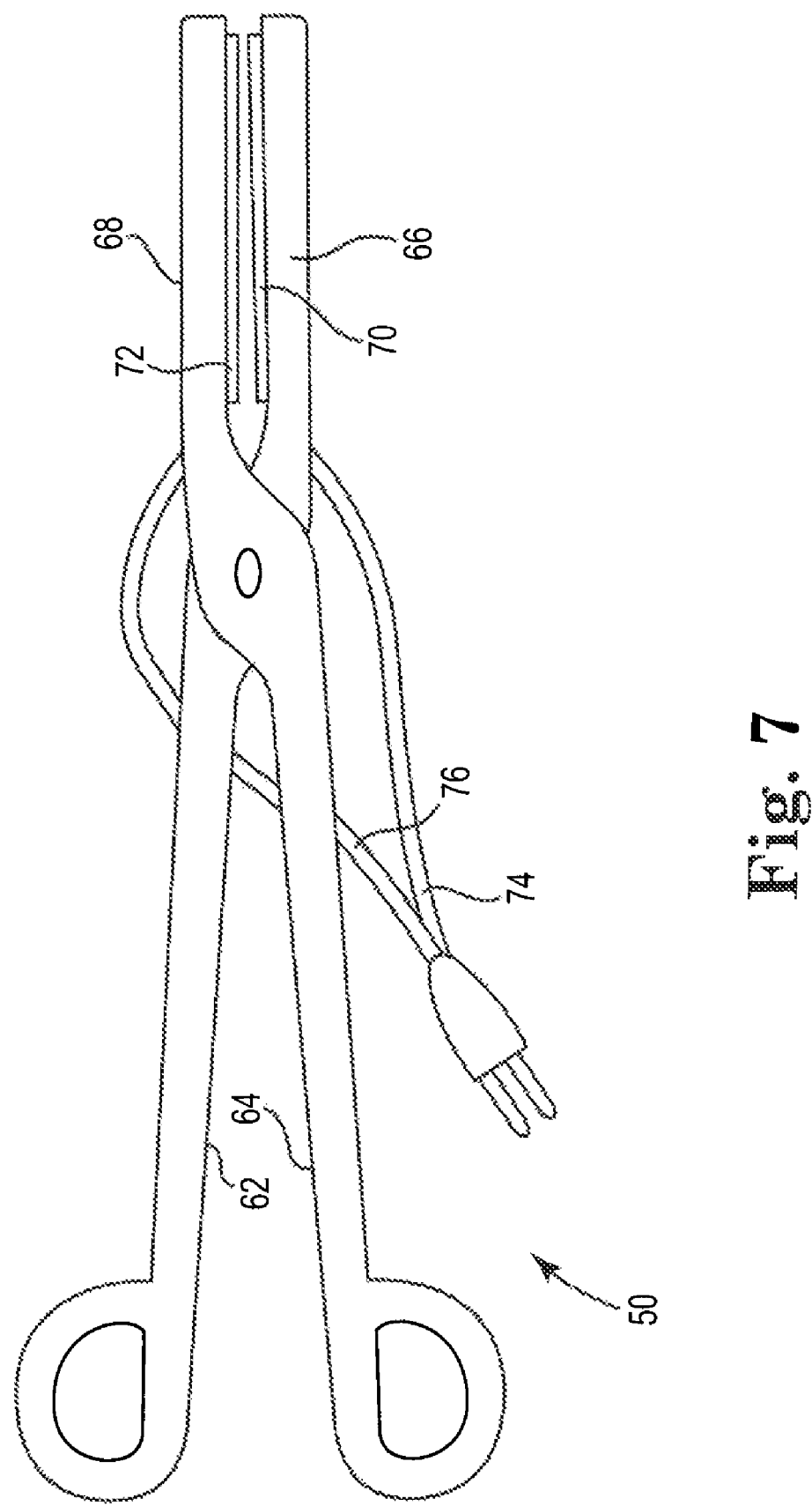
FIG. 7 is a side view of an ablation device useful with the system of FIG. 1.

Regardless of the particular format (and possible timing and/or modulation) of the high voltage, pulsed energy delivered by the pulse generator 22, the delivery instrument 24 and the electrodes 26 can assume a variety of forms. For example, FIG. 7 shows an ablation device 60 that may be used according to some embodiments of the present disclosure as the delivery instrument 24 (FIG. 1) and electroporation electrodes 26 (FIG. 1). The ablation device 60 is akin to a hemostat and generally comprises handles 62, 64 coupled to jaws 66, 68, respectively, that are moveable (e.g., pivotable, slidable, etc.) relative to one another. Located along the jaws 66, 68 are electroporation electrodes 70, 72 adapted for delivering the high density pulsed energy described above. Each electrode 70, 72 is provided with a conductor 74, 76 allowing the electrodes 70, 72 to be electrically coupled to the pulse generator 22 (FIG. 1).

The jaws 66, 68 can have a straight configuration as illustrated, or may be curved. Optionally, the jaws 66, 68 can carry an elongated magnet or series of magnets, extending along the electrodes 70, 72, to assist in aligning the electrodes 70, 72 as described in U.S. Pat. No. 6,699,240, the teachings of which are incorporated by reference. Regardless, the handles 62, 64 are operable by a surgeon to compress the electrodes 70, 72 (via pivoting of the jaws 66, 68) against opposite sides of cardiac tissue to be ablated. Alternatively, the hemostat-like configuration can assume various other designs and/or incorporate additional features such as those described in U.S. Publication No. 2008/0039746, the teachings of which are incorporated herein by reference. Additionally, while FIG. 7 reflects the jaws 66, 68 as being pivotably connected at a pivot point, in other constructions, the jaws 66, 68 are assembled so as to be parallel to one another and transversely slidable. With this alternative construction, a relatively uniform spacing is maintained between the jaws 66, 68, and thus the electrodes 70, 72, as the jaws 66, 68 are moved toward and away from one another.

In some embodiments, once the target site (e.g., right atrium, left atrium, epicardial surface, endocardial surface, etc.) is accessible, a user guides the jaws 66, 68 to the target site. Once the electrodes 70, 72 are located in a desired position, the electrodes 70, 72 are then energized with high voltage, pulsed energy for short durations as described above to induce cell electroporation and death at the tissue between the electrodes 70, 72. In related embodiments, the electrodes 70, 72 (otherwise reflected in FIG. 7 as each being a single, elongated electrode body) are replaced with a plurality of electrodes (e.g., a plurality of spaced electrodes are carried by the first jaw 66, and a corresponding number of similarly spaced electrodes are carried by the second jaw 68 to define electrode pairs between the jaws 66, 68). With this construction, different energy can be delivered to each electrode pair as a function, for example, of the tissue to be ablated. The variation(s) in energy delivered to each electrode pair can be in the form of any of the parameters described above (e.g., waveform, pulse width, voltage, amplitude, etc.), and can be adjusted over time. Even further, a pulse series can be timed across the electrode pairs (e.g., a first pulse electrode pair, a second pulse delivered to the next adjacent electrode pair, etc.).

Figure 8A:
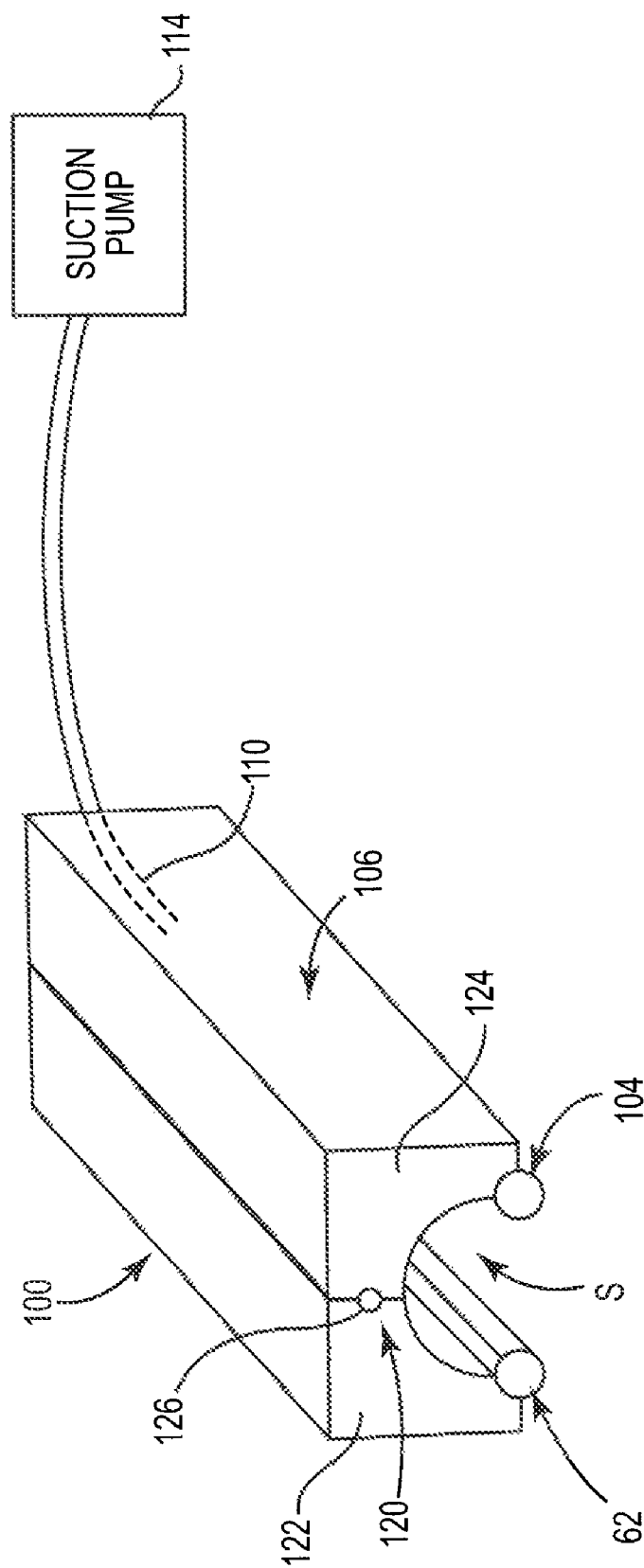
FIGS. 8A and 8B illustrate another ablation device useful with the system of FIG. 1.

The electroporation electrodes and corresponding delivery instrument can assume a wide variety of forms differing from those described above. For example, FIG. 8A illustrates a portion of an alternative electroporation ablation device including a delivery instrument 100 and electrodes 102, 104. The delivery instrument 100 includes a housing assembly 106 maintaining the electrodes 102, 104 such that the first electrode 102 is spaced from the second electrode 104 by a spacing S, with the housing assembly 106 forming a lumen 110 (referenced generally) extending from a distal opening 112 (best shown in FIG. 8B) that is fluidly open to the spacing S. With this in mind, the lumen 110 is fluidly connected to a vacuum source 114 (i.e., a suction pump) that operates to create a negative pressure at the spacing S. In general terms, during use, the vacuum source 114 is activated to draw tissue T (FIGS. 8C and 8D) into the spacing S, and thus intimately between the electrodes 102, 104.

Figure 8B:
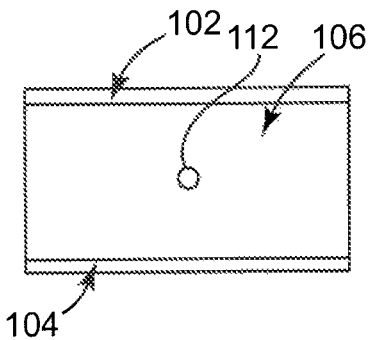
Figure 8C:
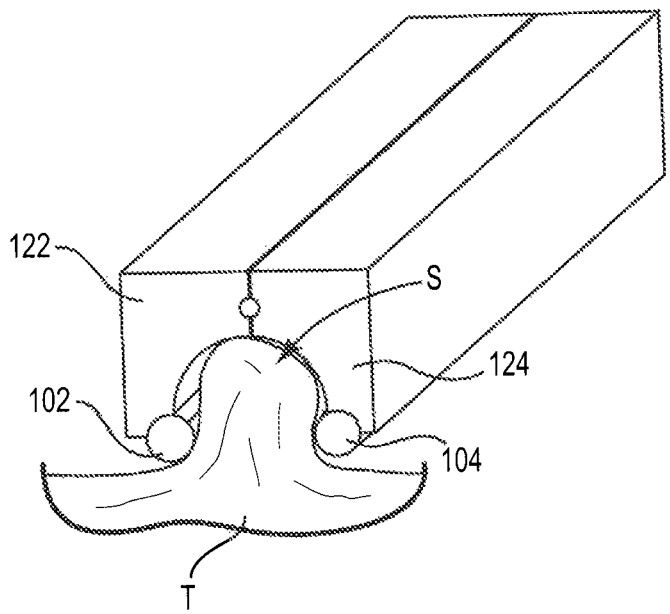
FIGS. 8C and 8D illustrate use of the device of FIG. 8A.
Figure 8D:
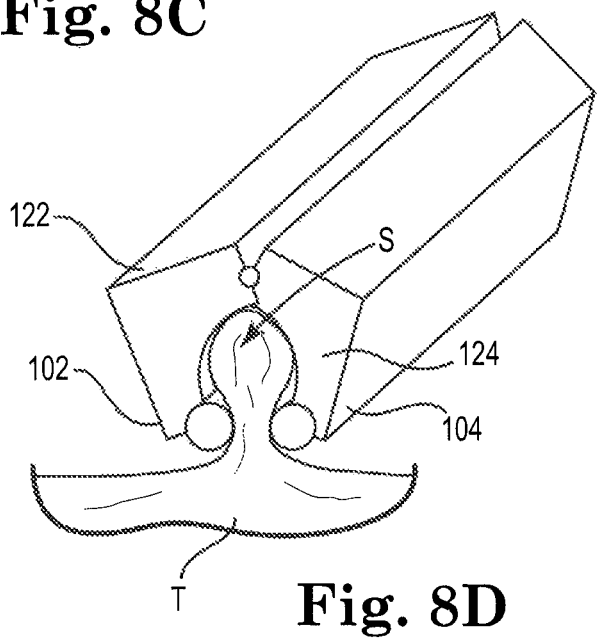

With the above configuration, and as best shown in FIG. 8B, the electrodes 102, 104 are linear electrodes, each defining a major axis. The housing assembly 106 arranges the electrodes 102, such that the major axes are substantially parallel to one another. In some embodiments, the linear electrodes 102, 104, have a length greater than a width, with the width of the electrodes 102, 104 in the range of 3-7 mm. It has surprisingly been found that with electroporation ablation applications, these orientations and dimensions effectuate desired irreversible cardiac cell electroporation with relatively narrow electrodes, and thus a relatively narrow resultant lesion. Further, drawing the tissue T into the spacing S between the electrodes 102, 104 brings the endocardial tissue on the shortest pathway between the electrodes 102, 104 (thus, highest current density). Therefore, a more complete transmural lesion across the tissue T can be made.

To further reduce the distance between the electrodes 102, 104, and thus the current density pathway, in some embodiments, the housing assembly 106 incorporates a clamping device 120 (referenced generally) including opposing legs 122, 124, and a hinge 126. The first leg 122 maintains the first electrode 102 and the second leg 124 maintains the second electrode 104. The hinge 126 effectuates a pivoting relationship between the legs 122, 124, and in particular the electrodes 102, 104 carried thereby. Thus, and as reflected in a transition of the housing assembly 106 from the orientation of FIG. 8C to the orientation of FIG. 8D, the spacing S between the electrodes 102, 104, can be reduced, thus forcing the tissue T between the electrodes 102, 104 to a reduced thickness.

Figure 9A:
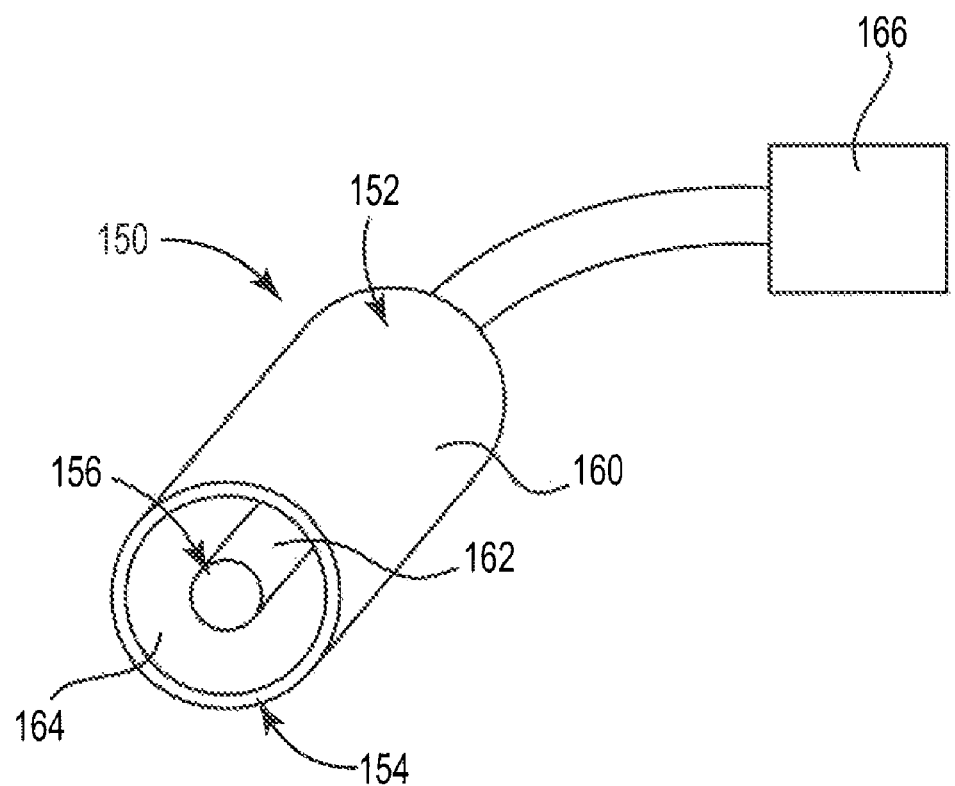
FIGS. 9A and 9B illustrate another ablation device useful with the system of FIG. 1.
Figure 9B:
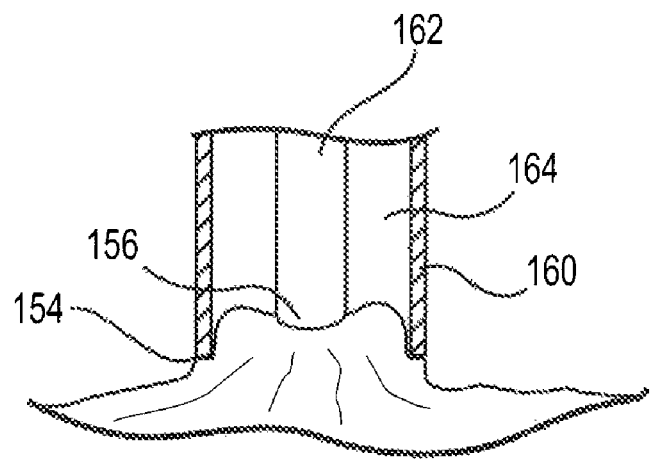

Another electroporation ablation device 150 is shown in FIGS. 9A and 9B. The device 150 includes a housing assembly 152 maintaining first and second electrodes 154, 156. The housing assembly 152 can be akin to a pen-type ablation instrument (e.g., a Cardioblate® instrument available from Medtronic, Inc., of Minneapolis, Minn.), and includes an outer member 160 and an inner member 162. The outer member 160 maintains the first electrode 154, whereas the inner member 162 maintains the second electrode 156. With this in mind, a lumen 164 is formed within the outer member 160, and is fluidly connected to a vacuum source 166.

With the one construction reflected in FIGS. 9A and 9B, the outer member 160 is tubular in nature, with the first electrode 154 having a ring-like shape. The second electrode 156 has a rounded shape (e.g., hemispherical) and is centrally maintained relative to the first, ring electrode 154. Further, and as best reflected in FIG. 7B, the second electrode 156 is proximally spaced relative to the first, ring electrode 154 (e.g., on the order of 1-10 mm).

During use, the housing assembly 152 is manipulated to position the first electrode 154 against tissue T to be ablated. The vacuum source 166 is then operated to generate a negative pressure within the lumen 164, drawing a section of the tissue T into the lumen 168, and into intimate contact with the second electrode 156. The electrodes 154, 156 are then operated as bipolar electrodes in delivering pulsed, high voltage electroporation ablation energy as described above. In this regard, the concentric arrangement of the second electrode 156 relative to the first electrode 154 better ensures even distribution of current density.

Returning to FIG. 1, regardless of an exact configuration of the delivery instrument 24, in some embodiments the electroporation electrodes 26 are formed of an electrically conductive metal that releases cytotoxic metal ions in the presence of pulsed energy. For example, with some constructions, the electroporation electrodes 26 are formed of a metal material such as nickel, silver, cobalt, cadmium, copper, tin, antimony, chromium, or aluminum. With these and similar metals, toxic ions are created in the presence of high voltage pulses that in turn are delivered to the target site tissue and accelerate the process of targeted cell death. In other embodiments, the system 20 is adapted to deliver a liquid agent in the form of toxic ionic concentrations or cytotoxic compound to the target tissue site during the delivery of the high voltage, pulsed energy. The so-delivered agent will then pass into the porated cells, again accelerating cell death. Alternatively, the systems and methods of the present disclosure can be practiced without the delivery of cytotoxic ions/compounds, such that the electroporation electrode constructions described above are optional.

In other embodiments, the electroporation electrodes 26 are formed or configured to mitigate or reduce thermal damage to tissue as part of a tissue ablation procedure. For example, the electroporation electrodes 26 can each be a high thermal mass material such as gold, platinum, and the like. Additionally or alternatively, the electroporation electrodes 26 can be cooled or irrigated.

The cardiac tissue ablation systems and methods of the present disclosure provide a marked improvement over previous designs. By employing pulsed, high voltage energy to effectuate IEP ablation of cardiac tissue cells, transmural lesions can be rapidly created at rates much less than those typically encountered with conventional RF energy ablation. Further, the applied current can be specifically directed, and it may be possible to design electrode arrays or shapes that can deliver very specific lesions patterns without the generation of excessive heat.

EXAMPLES

Extensive efforts have been made by the inventors to confirm an ability of systems and methods in accordance with the present disclosure to effectuate viable cardiac ablation via IEP.

Ex Vivo Study

An ex vivo swine skeletal muscle model was developed for evaluating cell death mechanism by measuring stimulated muscle force up to 24 hours. Skeletal muscle specimens from porcine rectus abdominis muscle biopsies were obtained and placed in oxygenated Krebs buffer. Immediately after removal, the muscle was placed in a dissection dish that was continuously oxygenated with carbogen (95% $O_2$ and 5% $CO_2$) at room temperature. The muscle specimens were affixed with small pins to the bottom of a dish lined with sylgard in order to fix the position of the muscle while it was further prepared. Connective tissue and fat was removed from the muscle with a fine scissors and forceps while the preparation was viewed through a dissecting microscope. Several smaller muscle bundles, with approximate dimensions of 2-4 cm in length and 2-3 mm in diameter were prepared, with care taken not to damage individual muscle fibers.

The bundles of fiber were mounted in the sample chamber by tying loops of suture to each end of the preparations. The sample chamber was water-jacketed, allowing the Krebs solution around the muscle to be maintained at 37 degrees Celsius. The composition of Krebs buffer was: NaCl (118.1 mM), KCl (3.4 mM), $KH_2PO_4$ (1.2 mM), $MgSO_4 7H_2O$ (1.0 mM), Dextrose (10.8 mM), $NaHCO_3$ (25.0 mM), and $CaC_2$ (2.5 mM).

Initial twitch force was assessed and bundles that did not elicit viable twitches (<1 g peak force) were excluded. The optimal length of muscle bundles was determined by stretching the muscle using a micromanipulator that was connected to a force transducer. The bundles were activated by field stimulation using a pair of platinum electrodes that extended the length of the preparation. The voltages applied to each bath were increased to allow for stimulation of each isolated bundle. The muscle was simultaneously stimulated with pulses of 1 millisecond (ms) at a frequency of 0.1 Hz. The amplitudes of the contraction were measured in grams and signals from the force transducer were amplified and recorded using LabVIEW 3.0 software. The optimal length for each preparation was determined as to when the peak twitch amplitude was maximal and did not change after the muscle had been further stretched. Various electroporation ablation energies were applied as described below. At hours 1, 2, 3, and 4, each of the muscle bundle post-ablation forces as well as baseline were normalized using the muscle bundles pre-ablation force as a baseline.

The wet weight and the length of each muscle bundle were measured and recorded. The area of the muscle was calculated by dividing the weight of the muscle by the product of the known density of muscle (1.056 g/cm$^3$) times the muscle length. These values were used to estimate bundle cross-sectional areas. All the twitch forces were then normalized by cross-section area of muscle bundles.

High voltage electrical pulses were applied to ablate dissected rectus abdominus muscle using a bipolar clamp with dry linear electrodes (e.g., akin to the ablation device 60 of FIG. 7). Study samples were subjected to either high voltage, short burst electroporation ablation energy or RF ablation energy. For either ablation energy type, the same bi-polar clamp was applied transversely to the longitudinal direction of the muscle. Control muscle bundles had a bi-polar clamp applied in the same manner with the exception of applied energy. The pulse generator used was an in-house generator akin to the pulse generator 22' of FIGS. 2A and 2B, capable of delivering a wide range of arbitrary burst pulses (minimum pulse width of 1 μs and interpulse interval 10 μs) and in both monophasic and biphasic mode.

Test specimens were divided into groups of no ablation ("control"), electroporation ablation ("IEP"), or RF ablation ("RF"). The IEP and RF groups were further subjected to differing energy formats as provided in Table 1 below.

TABLE 1

| Sample Group | Input Parameter Used | |
|---|---|---|
| Group 1 | Control | |
| Group 2 | Voltage (V) | 120 |
| (High IEP) | Pulse width (μs) | 200 |
| | Duty cycle (%) | 50 |
| | Polarity | Monophasic |
| | Total time energy delivered (μs) | 10,000 |
| | Pulses per train | 50 |
| | Number of trains | 1 |
| Group 3 | Voltage (V) | 10 |
| (Low IEP) | Pulse width (μs) | 200 |
| | Duty cycle (%) | 50 |
| | Polarity | Monophasic |
| | Total time energy delivered (μs) | 10,000 |
| | Pulses per train | 50 |
| | Number of trains | 1 |
| Group 4 | Power (W) | 25 |
| (High RF) | Time energy delivered (sec) | 20 |
| Group 5 | Power (W) | 1 |
| (Low RF) | Time energy delivered (sec) | 5 |

Figure 10:
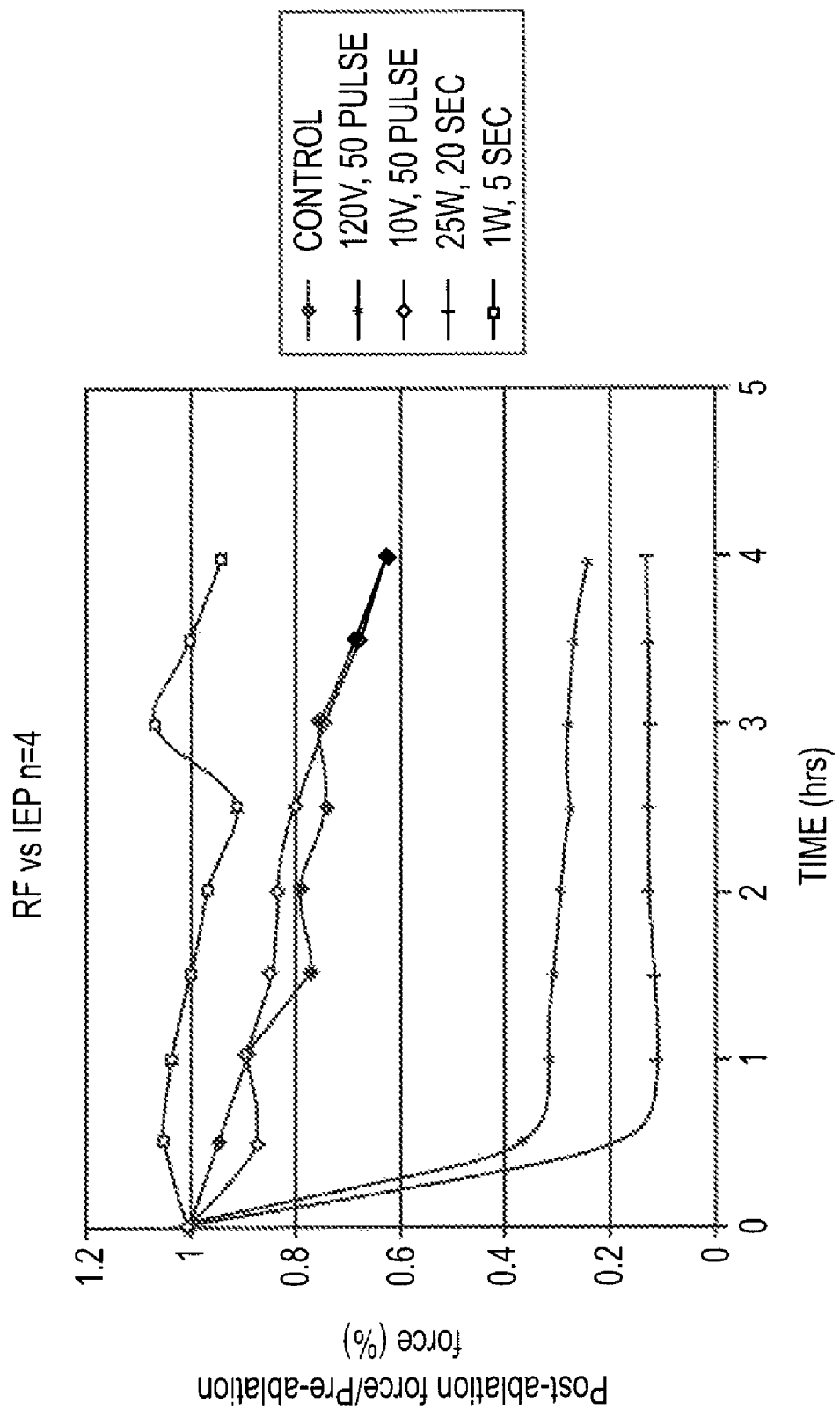
FIG. 10 is a graph plotting measured muscle forces in connection with an ex vivo study comparing electroporation ablation and RF ablation.

The muscle bundle pre-ablation forces were measured as described above, and muscle bundle post-ablation forces were measured hourly for four hours following ablation. The measured forces at each hour are plotted in FIG. 10 as a function of percent change in force. It was observed that at hours 1-4, Groups 2 (High IEP) and 4 (High RF) had significantly lower post-ablation forces compared to any other group. At hours 1-4, Group 2 (High IEP) had significantly lower post-ablation forces compared to Group 5 (High RF). At hours 1-3, Group 2 (High IEP) had significantly larger post-ablation forces compared to Group 4 (High RF). At hour 4, the Groups were not significantly different. At hours 1-4, Group 2 (High IEP) had significantly lower post-ablation forces compared to Group 3 (Low IEP). At hours 1-4, Group 4 (High RF) had significantly lower post-ablation forces compared to Group 5 (Low RF).

Figure 11:
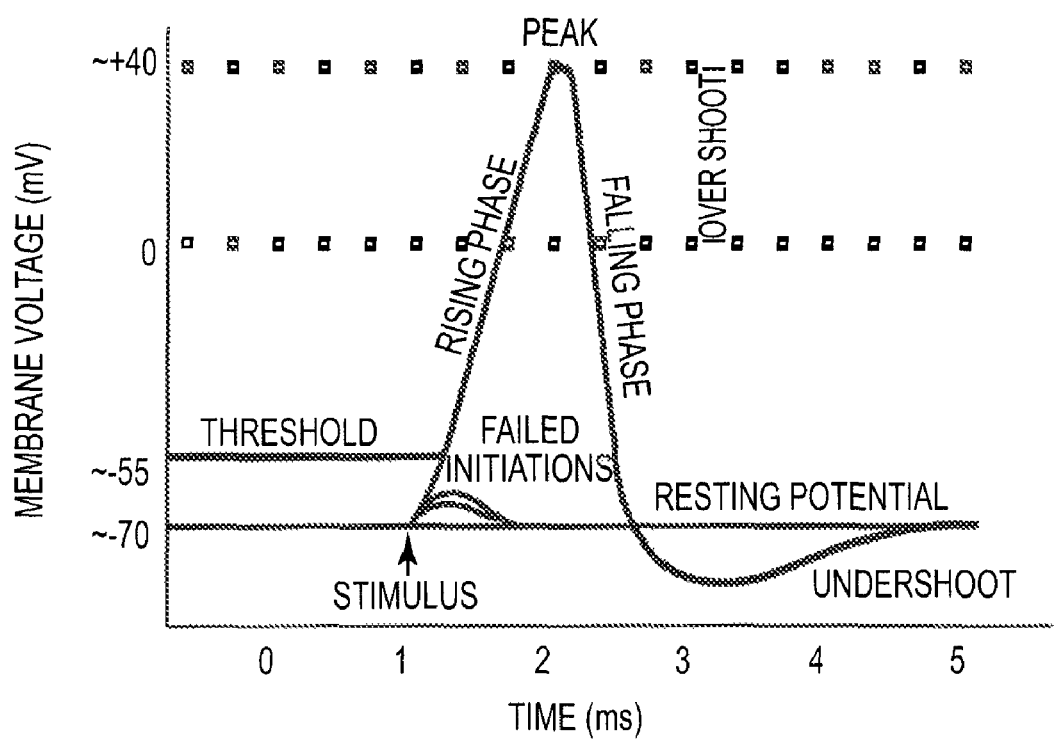
FIG. 11 is a graph illustrating cell membrane depolarization in response to an applied electroporation voltage.

It was determined that application of IEP and RF energy caused significant muscle force reduction. However, post-IEP and post-RF muscle bundles did not lose contractility completely throughout the experimental period (approximately 4.5 hours). IEP induces immediate membrane pores with a certain degree of cell damage however it requires time until it reaches complete cell death. During this period, ions located in and out of the cell transfer through IEP-induced membrane pores; this free ion exchange depolarizes cell membrane, gradually increasing the resting membrane potential from −70 mV to 0V. As a result, the relative peak voltage of action potential is decreased (FIG. 11) leading to lower twitch force response.

Figure 12:
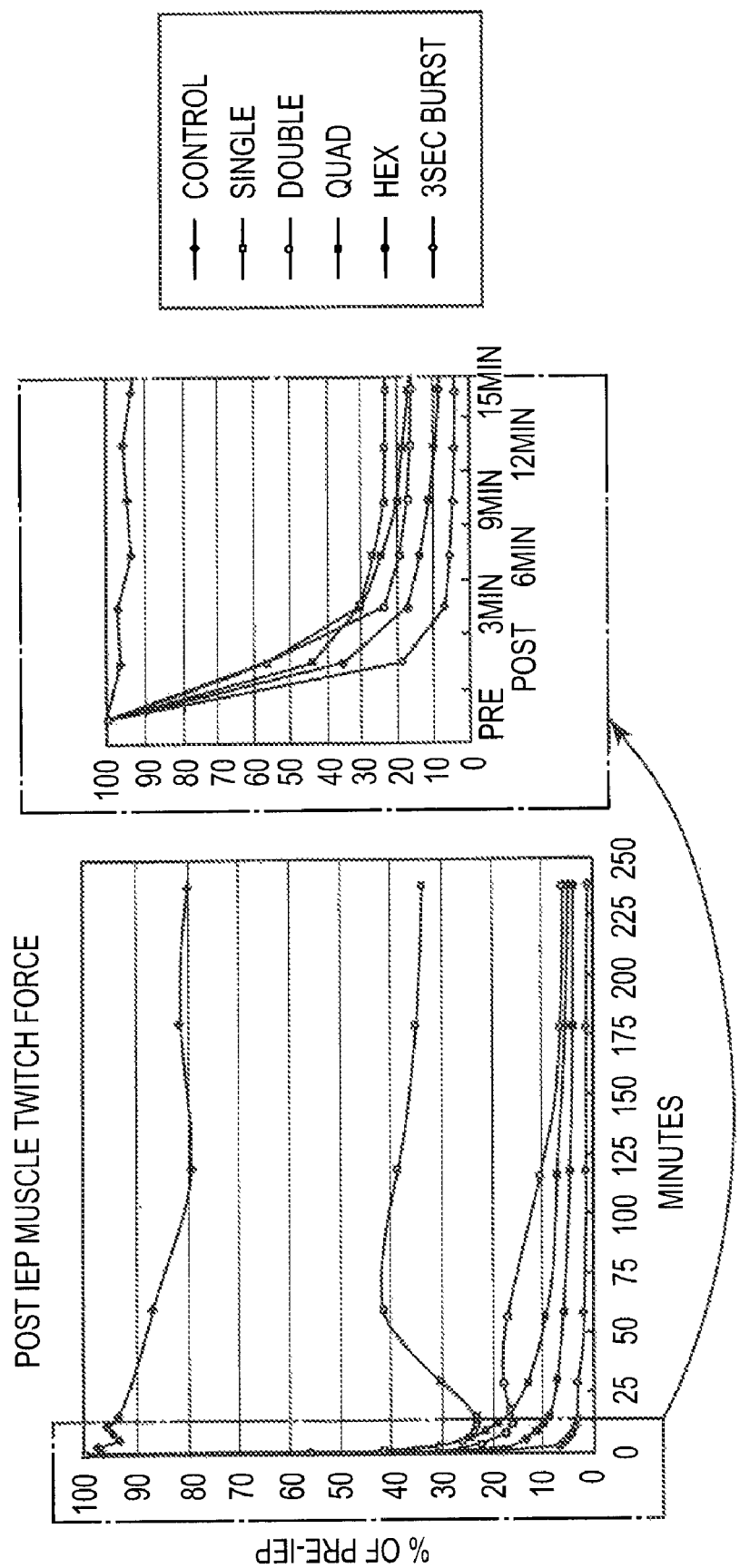
FIG. 12 is a graph illustrating measured muscle twitch forces in response to various electroporation energy formats.

Also, a clear dose-response trends with the amount of IEP energy relating to muscle force reduction was found. FIG. 12 shows a comparison between different number of trains. Higher energy causes larger degree of cell damage and/or larger number of pores, which provides higher chance of ion transfer in and out of the cell. Therefore, higher IEP energy ablation facilitates cell death which is the result of ion imbalance between the inside and outside of the cell membrane as compared to lower energy ablation.

Pointedly, the single train pulse IEP Groups showed a trend of muscle recovery. At an applied voltage of 40V (100V/cm), there appears to be a threshold that directly relates voltage applied to the force output of the muscle bundle. Study Groups with less than 40V do not appear to effect post-ablation force, while study Groups with greater than 40V influenced post-ablation force greatly.

For both the RF and IEP groups, threshold values were not achieved. The low-dose RF and IEP groups (Group 5, Group 3) behaved statistically the same as the Control Group for the entirety of the study. This indicates that the dose response was not large enough to elicit a decline in post-ablation force that deviated from the Control Group. On the opposite end of the spectrum, there are the other study groups (Group 4, Group 2) which have significantly lower post-ablation forces from the Control, Group 5, and Group 3 for the entirety of the study.

When compared with each other, the high dose RF group (Group 4) elicited a significantly larger post-ablation decrease than the high dose IEP group (Group 2) from hours 1-3. However, at hour 4 the high-dose groups were statistically the same.

In Vivo Study

To investigate methods of lesion identification, acute and chronic animal studies were performed in a sheep model.

The efficacy of IEP ablation was evaluated by chronic monitoring of ablations performed on the atrial appendages, superior vena cava, and pulmonary veins. Clamp IEP ablations were performed (i.e., using an ablation device akin to the clamp ablation device 60 of FIG. 7) to isolate the distal right atrial appendage (RAA) in the chronic animals. The RAA in sheep have a large (1-2 cm diameter, 2-4 mm thick) fat pad on the medial side of the distal tip that makes the RAA more challenging to ablate transmurally than the left atrial appendage LAA. The applied RAA energy format is shown in Table 2 below. A Model 4968 pacing lead (from Medtronic, Inc.) was placed distal and proximal to each RAA isolation lesion to allow chronic conduction exit block testing. Each lead was connected to a percutaneous test adapter (PTA) that was implanted under the skin to allow periodic monopolar pacing to be performed to each lead through needles inserted through the skin into the PTA connections. Pacing to check conduction block was performed at the following time points (and at termination if terminated between time points): During surgery and post implant after wound closure; and 1, 2, 4, 6, 8, 10 and 12 weeks post-surgery.

TABLE 2

| Sample | Device | Lesion | Voltage | Pulses | Pulse Width (ms)/Total # Pulses | Impedance | Comments |
|---|---|---|---|---|---|---|---|
| C1 | Clamp | RAA | 415 V | 10 pulses for 3 sec at 5 Hz | 0.2/150 | N/A | Actual energy <25% |
| C2 | Clamp | RAA | 650-500 V | 40 pulses for 3 sec at 1 Hz | 0.2/120 | N/A | Arcing × 5 <10% |
| C3 | Clamp | RAA | 700 V | 10 pulses for 3 sec at 5 Hz | 0.2/150 | 137 Ω | Actual energy <25% |
| C4 | Clamp | RAA | 485 V | 50 pulses for 5 sec at 2 Hz | 0.2/500 | 105 | Actual energy 50% |
| C5 | Clamp | RAA | 600 V | 10 pulses for 3 sec at 5 Hz | 0.2/150 | 160 Ω | Actual energy <25% |
| C6 | Clamp | RAA | 645 V | 40 pulses for 5 sec at 1 Hz | 0.2/200 | 74 Ω | Actual energy 50% |
| C7 | Clamp | RAA | 600 V | 50 pulses for 5 sec at 1 Hz | 0.2/250 | 78 Ω | Actual energy 50% |
| C8 | Clamp | RAA | 500 V | 20 pulses for 5 sec at 1 Hz (biphasic) | 0.1/100 | N/A | Actual energy 95% |
| C9 | Clamp | RAA | 450 V | 40 pulses for 5 sec at 1 Hz (biphasic) | 0.1/200 | 80 Ω | Actual energy 95% |

Figure 13:
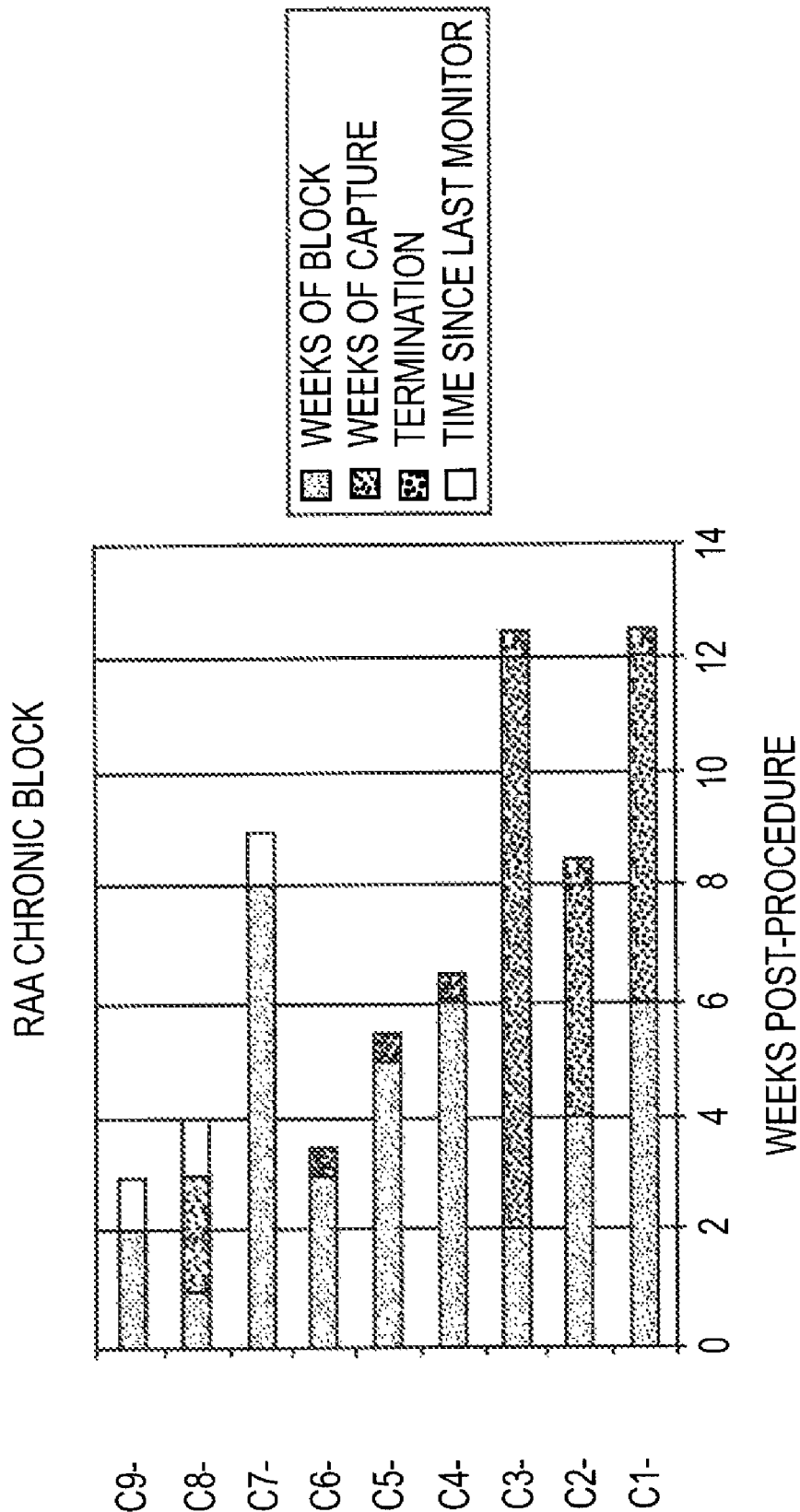
FIG. 13 is a plot of conduction block monitoring of chronic heart samples subjected to electroporation energy at the distal right atrial appendage in connection with an in vivo study.

The results of the periodic pacing monitors to evaluate conduction block are reflected in FIG. 13.

An examination of the gross pathology and histology of the chronic ablations for specimen C2 revealed transmural lesions, and all five cross-sections through the ablation showed a band of either transmural fibrosis or fatty infiltration with the thickest wall being 3.47 mm. Small clusters of viable myocardial cells were sparsely present in some of the cross-sections.

In addition to the RAA sites, the LAA was isolated in several chronic animals using the energy parameters provided in Table 3 below. Results of the LAA conduction block monitoring are graphed in FIG. 14. Histological examinations of these LAA lesions showed all ablation line cross-sections to be transmural.

TABLE 3

| Sample | Device | Lesion | Voltage | Pulses | Pulse Width (ms)/Total # Pulses | Impedance | Comments |
|---|---|---|---|---|---|---|---|
| C1 | Clamp | LAA | 415 V | 10 pulses for 3 sec at 5 Hz | 0.2/150 | N/A | Actual energy <25% |
| C2 | Clamp | LAA | 650 V | 40 pulses for 3 sec at 1 Hz | 0.2/120 | N/A | Arcing × 5 <50% |
| C3 | Clamp | LAA | 480 V | 50 pulses for 5 sec at 1 Hz | 0.2/250 | 73 Ω | Actual energy <50% |
| C4 | Clamp | LAA | 410 V | 50 pulses for 4 sec at 3 Hz | 0.2/600 | 67 | Actual energy 25% |
| C9 | Clamp | LAA | 450 V | 40 pulses for 5 sec at 1 Hz (biphasic) | 0.1/200 | 140 Ω | Actual energy 25% |

Additional clamp ablations were performed on other locations in the chronic animals including the superior vena cava (SVC), inferior vena cava (IVC), distal vena cavae, left pulmonary vein (LPV), right pulmonary vein (RPV), caudal PV (CPV), and esophagus. Conduction block was checked acutely in these locations and conduction block could be achieved in nearly all cases (94.5% for acute animals (n=37) and 96.2% for chronic animals (n=27)). For the chronic animals, pacing leads were placed on at least one of the atrial appendages.

At termination of the chronic animals, an EP catheter was introduced to evaluate entrance block of the SVC, IVC, RAA, and freewall lesions. Lesions were marked at surgery using U-clips so these were located fluoroscopically and the catheter guided to the site. In all four terminated chronic animals, the catheter EGM signals appeared to confirm that local conduction ended at the SVC, IVC, or RAA lesion site. Exit block testing was performed on only appendages where pacing leads were implanted. This was confirmed histologically. The major diagnosis was transmural replacement fibrosis and fatty infiltration.

From the in vivo study, it was determined by both conduction block and histology that transmural lesions were created in myocardium that lies under layers of epicardial fat using both clamp and probe delivery devices delivering short bursts of high voltage ablation energy. Every lesion created on the distal RAA was placed over a fat pad that typically ranged from 2-4 mm thick.

Epicardial IEP ablation was found to create atrial free-wall or connecting lesions, based on both acute and chronic results. In particular, pen-type ablation devices were used to "draw" lesion lines around an "island" of tissue, and long-term conduction blocks were found.

In addition to free-wall island lesions, a total of seven connecting lesions were performed (LA dome and PV connecting lesions) using probe-type device. Initial evaluation of local EGM measurement on the lesion site confirmed loss of EGM signals.

Gross pathology and histological evaluation have shown the bipolar clamp and bipolar probe lesions to have very well defined lesion boundaries in conjunction with electroporation energy.

Possible IEP-caused stenosis or aneurysm of ablated great vessels was also evaluated. A total of 60 vena cavae ablations were created, 20 of which were on chronic animals, as well as 26 PV isolation lesions, 13 in chronics. In all of these lesions, absolutely no sign of stenosis or narrowing of any ablated great vessel was seen. These same tissues were evaluated histologically and were noted to have remained physically unremarkable at the lesion sites with no signs of constriction or vessel wall shrinkage. The main characteristic of myofibers after acute IEP is the formation of contraction bands and a mild swelling of the cells. The hypercontractions may result in myofiber break-up. This is easier to appreciate in ventricular or esophageal myofibers than in the atrium. In contrast to RF lesion, this change was found to be homogenous throughout the target zone. RF lesions were found to present a distinct zoning: a peripheral rim with contraction bands lacking myofiber break-up, and a central part with coagulation necrosis.

These cells were, in contrast to IEP delivery, shrunken and all were purple discolored in the Trichrome Masson stain. However, purple discoloration of myofibers was also found on many IEP ablations.

To evaluate possible effect of IEP cardiac ablation on the esophagus, direct ablation of the esophagus was performed. It was found that IEP energy, when applied directly to the esophagus, may cause only necrosis of the muscular layers while leaving the endothelial lining relatively unaffected. Conversely, in the esophagus, the RF control ablation penetrated adventitia, muscle layer (composed of skeletal muscle), submucosa, and the epithelium. For the IEP ablation, lesions were especially restricted to the muscle layer only. Intentional esophageal ablations, either by clamp or probe, were barely visible from the adventitia for IEP energy delivery, but were easily detectable after RF ablation. The luminal surface in all IEP animals was normal, but displayed a prominent pale yellow band corresponding to the RF ablation. IEP lesions could be felt by palpation as indistinct tissue swelling. Similar band-like swelling was also felt in several caval IEP ablations.

From the above, it was concluded that IEP ablation is feasible. Its efficacy was confirmed with the creation of transmural lesions on various areas of the heart, including connecting lesions, while observing minimal safety concerns. The following, possible complications of cardiac ablations were not detected: pericardial tamponade from cardiac perforation, massive atrial thrombosis, endocardial ulceration beneath the ablations, myocardial infarction, venous stenosis or strictures, valvular damage, perforating esophagus or aortic injury, or phrenic nerve injury.

All publications, patents, and patent applications are incorporated herein by reference. While the foregoing specification of this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A cardiac tissue electroporation ablation system comprising:
    a delivery instrument maintaining at least one electroporation electrode; and
    an electrical pulse generator electrically connected to the at least one electroporation electrode;
    wherein the pulse generator is programmed to deliver pulsed, high voltage biphasic energy to the electroporation electrode sufficient to induce IEP ablation of cardiac tissue cells, including an output voltage in the range of 200-700 volts, a pulse width in the range of 50-200 microseconds, a pulse interval in the range of 100-400 microseconds, and as a series of pulse trains over a range of 2-6 seconds with a train interval in the range of 250-1,000 milliseconds.

2. The system of claim 1, wherein each pulse train includes 20-60 biphasic pulses.

3. The system of claim 1, wherein the at least one electrode is formed of a metal material constructed to release cytotoxic metal ions in the presence of pulsed energy.

4. The system of claim 3, wherein the metal material is selected from the group consisting of nickel, silver, cobalt, cadmium, copper, tin, antimony, chromium, and aluminum.

* * * * *